United States Patent [19]
Grohe et al.

[11] Patent Number: 5,300,643
[45] Date of Patent: Apr. 5, 1994

[54] QUINOLONECARBOXYLIC ACID DERIVATIVES

[75] Inventors: Klaus Grohe, Odenthal; Wolfgang Dummer, Cologne; Kai Rossen, Leverkusen; Arnold Paessens, Haan, all of Fed. Rep. of Germany

[73] Assignee: Bayer Aktiengesellschaft, Leverkusen, Fed. Rep. of Germany

[21] Appl. No.: 935,627

[22] Filed: Aug. 25, 1992

Related U.S. Application Data

[62] Division of Ser. No. 585,580, Sep. 19, 1990, Pat. No. 5,217,972.

[30] Foreign Application Priority Data

Oct. 12, 1989 [DE] Fed. Rep. of Germany ....... 3934082

[51] Int. Cl.$^5$ ................. C07D 401/10; C07D 413/10; C07D 417/10
[52] U.S. Cl. .................................. 544/363; 544/58.6; 544/128; 544/357; 546/156
[58] Field of Search ...................... 544/363, 58.6, 128; 546/156

[56] References Cited

U.S. PATENT DOCUMENTS 4,704,459 11/1987 Todo et al. ......................... 546/123
4,851,535 7/1989 Todo et al. ........................... 546/25

FOREIGN PATENT DOCUMENTS 0302372 7/1988 European Pat. Off. .

OTHER PUBLICATIONS

E. Ferrazzi, "Antiviral Activity of Gyrase Inhibitors Norfloxacin, Coumermycin A and Nalidixic Acid," in *Biochemical Pharmacology*, vol. 37, No. 9, 1988, pp. 1885–1886.
Beilsteins Handbuch, vols. 2 and 3, 1921, pp. 38–40.
Beilsteins Handbuch, vols. 23 and 27, 1936, pp. 4–6, 8. vol. 27, p. 5 pp. 166–174.

*Primary Examiner*—Alan L. Rotman
*Assistant Examiner*—James H. Turnipseed
*Attorney, Agent, or Firm*—Sprung Horn Kramer & Woods

[57] ABSTRACT

New quinolone-carboxylic acids of the general formula (I)

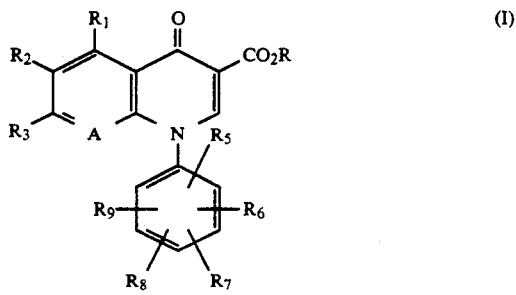

wherein the definitions for $R_1$–$R_9$ are given in the description, a process for their preparation and their use as medicaments, in particular as antiviral agents.

4 Claims, No Drawings

QUINOLONECARBOXYLIC ACID DERIVATIVES

This is a division of U.S. application Ser. No. 585,580, filed Sep. 19, 1990, now U.S. Pat. No. 5,217,972.

The present invention relates to new quinolone-carboxylic acid derivatives, to a process for their preparation and to their use as medicoments, in particular as antiviral agents.

It is known that some quinolonecarboxylic acid derivatives have excellent antibacterial activity. Little has hitherto been disclosed about the antiviral action of quinolones. Thus E. Ferrazzi et al. described the antiviral action of norfloxacin, coumermycin $A_1$ and nalidixic acid against BK viruses which belong to the papovaviruses (Biochemical Pharmacology, Vol. 37, No. 9, pp. 1885–1886, 1986).

At the 5th AIDS conference in Montreal, Canada, L. Gurtler et. al. reported on the inhibition of HIV reverse transcriptase by ofloxacin, ciprofloxacin and norfloxacin (Abstract C. 624).

it has now been found that compounds of the general formula (I)

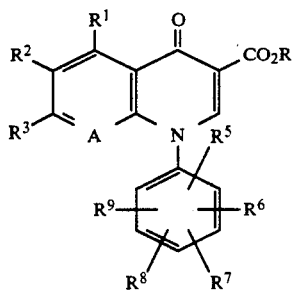

in which

R represents hydrogen or alkyl having 1–4 carbon atoms,

R represents hydrogen, amino, alkylamino having 1 to 4 carbon atoms, dialkylamino having 1 to 3 carbon atoms per alkyl group, hydroxyl, alkoxy having 1 to 4 carbon atoms, mercapto, alkylthio having 1 to 4 carbon atoms, arylthio, halogen, cyano or nitro, $R^2$ represents hydrogen, nitro or halogen, $R^3$ and $R^5$ are identical or different and represent $NR^{25}R^{26}$, in which $R^{25}$ and $R^{26}$ are identical or different and represent hydrogen, $C_1$–$C_{20}$-alkyl, optionally substituted by one or more halogens, OH, O-alkyl ($C_1$–$C_6$), alkyl ($C_1$–$C_4$), CN, or Coo alkyl ($C_1$–$C_6$), hydroxyl, or amino, alkylamino having 1–4 carbon atoms, dialkylamino having 1–3 carbon atoms per alkyl group or phenyl which is optionally substituted by halogen, or represent a group having the formula (II)

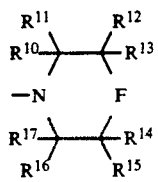

in which

F denotes O, S, $NR^{18}$ or $CR^{19}R^{20}$ and $R^6$, $R^7$, $R^8$ and R are identical or different and represent hydrogen, methyl, ethyl, nitro, amino, monoalkylamino having 1–3 C atoms, dialkylamino having 1–4 C atoms, methoxy, ethoxy, thiomethyl, thioethyl, trifluoromethyl, cyano or halogen, $R^{18}$ represents H, ($C_1$–$C_{10}$)-alkyl or ($C_3$–$C_6$)-cycloalkyl, optionally substituted by one or more substituents Hal, OH, CN, COOR or OR where R=($C_1$–$C_7$)-alkyl, aryl ($C_6$–$C_{12}$), optionally substituted by halogen, —O-alkyl ($C_1$–$C_2$) or ($C_1$–$C_4$)-alkyl,

CN,

COOalkyl ($C_1$–$C_4$), $C_1$–$C_4$-acyl or ($C_1$–$C_4$)-alkyl-sulphonyl, $R^{10}$, $R^{11}$, $R^{12}$, $R^{13}$, $R^{14}$, $R^{15}$, $R^{16}$, $R^{17}$, $R^{19}$ and $R^{20}$ are identical or different and represent hydrogen, $C_1$–$C_3$ alkyl or $C_3$–$C_6$-cycloalkyl, optionally substituted by one or more halogens, OH, O-alkyl ($C_1$–$C_6$), alkyl ($C_1$–$C_4$), CN or COO alkyl ($C_1$–$C_6$), hydroxyl, or amino, alkylamino having 1–4 carbon atoms, dialkylamino having 1–3 carbon atoms per alkyl group or phenyl which is optionally substituted by halogen.

$R^3$ and $R^5$ may further represent a radical of the structure (IV)

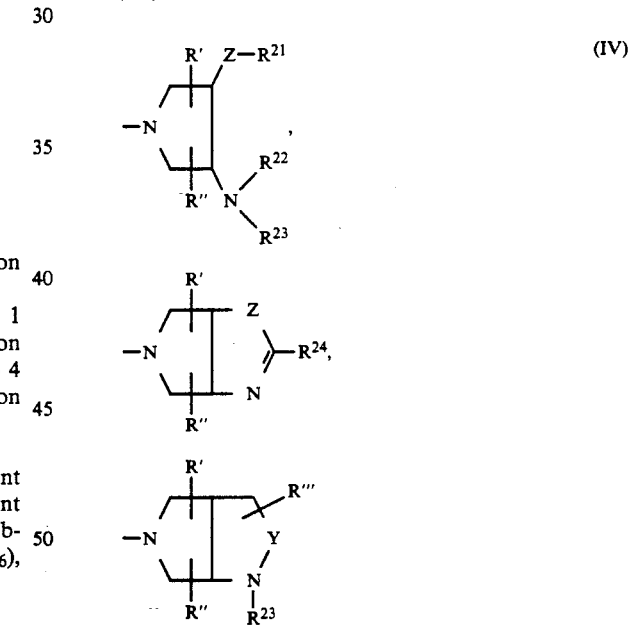

where $R^{21}$ can represent H, $C_1$–$C_4$-alkyl, aryl, or $C_1$–$C_4$-acyl, $R^{22}$ can represent H, $C_1$–$C_4$-alkyl, OH or $OCH_3$, where $R^{21}$ and $R^{22}$ can together also denote a $C_1$–$C_3$-alkylene bridge which is optionally monosubstituted or disubstituted by methyl, $R^{23}$ can represent H, $C_1$–$C_4$-alkyl, aryl, heteroaryl, benzyl, $C_1$–$C_4$-alkoxycarbonyl, $C_1$–$C_4$-acyl or (5-methyl-2-oxo-1,3-dioxol-4-yl)-methyl, $R^{24}$ can represent H, $C_1$–$C_4$-alkyl, R' can represent H, $CH_3$ or phenyl, R" can represent H, $CH_3$ or phenyl, R''' can represent H or $CH_3$, Y can represent O, CH₂, CH₂CH₂ or CH₂-O where the linkage of the CH₂-O group to the nitrogen can take place both via O and via CH₂, Z can represent O or S, ZR²¹ can represent hydrogen A represents N or CR₄, where R⁴ represents hydrogen, halogen, methyl, cyano, nitro, methoxy or amine or, alternatively, represents a bridge via O, S or CH₂ which is connected to the ortho-position of the phenyl ring at N-1.

R⁶, R⁷, R⁸ and R⁹ may be identical or different and represent hydrogen, alkyl having 1 to 5 carbon atoms, nitro, amino, monoalkylamino having 1-3 C atoms, dialkylamino having 1-6 C atoms, O-alkyl having 5 carbon atoms, S-alkyl having 1-5 carbon atoms, trifluoromethyl, cyano or halogen.

Preferred compounds in this connection are those of the general formula (I)

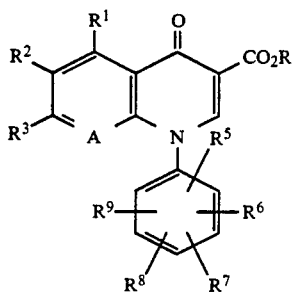

(I)

in which

R represents hydrogen, methyl or ethyl,

R¹ represents hydrogen, amino, nitro, methoxy, methylthio, cyano or halogen,

R² represents hydrogen, nitro or halogen,

R³ and R⁵ are identical or different and represent NR²⁵R²⁶, in which R²⁵ and R²⁶ are identical or different and represent hydrogen, C₁-C₂₀-alkyl, optionally substituted by one or more halogens, O-alkyl (C₁-C₆), alkyl (C₁-C₄), CN, or COO alkyl (C₁-C₆), hydroxyl, or amino, alkylamino having 1-4 carbon atoms, dialkylamino having 1-3 carbon atoms per alkyl group or phenyl which is optionally substituted by halogen, or represent a group having the formula (II)

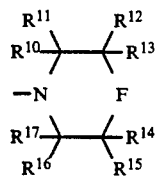

(II)

where

F denotes sulphur, oxygen, nitrogen, NR¹⁸ or CR¹⁹R²⁰ and

R¹⁸ represents

H, (C₁-C₁₀)-alkyl or (C₃-C₆)-cycloalkyl, optionally substituted by one or more substituents Hal, OH, CN, COOR or OR where R=(C₁-C₇)-alkyl, aryl (C₆-C₁₂), optionally substituted by halogen, —O-alkyl(C₁-C₂) or (C₁-C₄)-alkyl,

CN,

COOalkyl (C₁-C₄),

C₁-C₄-acyl or (C₁-C₄)-alkyl-sulphonyl,

R¹⁰, R¹¹, R¹², R¹³, R¹⁴, R¹⁵, R¹⁶, R¹⁷, R¹⁹ and R²⁰ are identical or different and represent hydrogen, C₁-C₃ alkyl or C₃-C₆-cycloalkyl, optionally substituted by one or more halogens, OH, methoxy, ethoxy, methyl, ethyl, cyano or CO₂Me, hydroxyl, or amino, alkylamino having 1-4 carbon atoms, dialkylamino having 1-3 carbon atoms per alkyl group or phenyl which is optionally substituted by halogen, R³ and R⁵ may further represent a radical of the structures

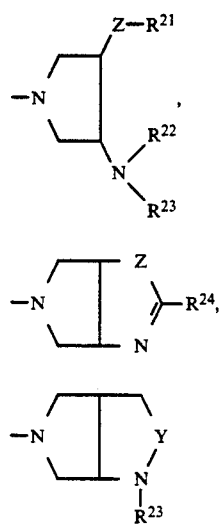

(IV)

where

R²¹ can represent H, C₁-C₄-alkyl, aryl, or C₁-C₄-acyl,

R²² can represent H, C₁-C₄-alkyl, OH or OCH₃, where R²¹ and R²² together can also denote a C₁-C₃-alkylene bridge which is optionally monosubstituted or disubstituted by methyl, R²³ can represent H, C₁-C₄-alkyl, aryl, heteroaryl, benzyl, C₁-C₄-alkoxycarbonyl or C₁-C₄-acyl, R²⁴ can represent H or C₁-C₄-alkyl, Y can represent O, CH₂, CH₂CH₂ or CH₂-O, where the linkage of the CH₂-O group to the nitrogen can take place both via O and via CH₂, Z can represent O or S, ZR² can represent hydrogen, A represents N or CR₄, where R⁴ represents hydrogen, halogen, methyl, cyano, nitro, methoxy or amine or, alternatively, represents a bridge via O, S or CH₂, which is connected to the ortho-position of the phenyl ring at N-1.

R⁶, R⁷, R⁸ and R⁹ are identical or different and represent hydrogen, methyl, ethyl, nitro, amino, monoalkylamino having 1-3 C atoms, dialkylamino having 1-4 C atoms, methoxy, ethoxy, thiomethyl, thioethyl, trifluoromethyl, cyano or halogen.

Particularly preferred in this connection are compounds of the general formula (I)

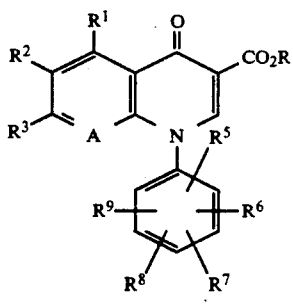

(I)

in which

R represents hydrogen, methyl or ethyl, $R^1$ represents hydrogen or halogen, $R^2$ represents fluorine, nitro or hydrogen, $R^3$ and $R^5$ are identical or different and represent $NR^{25}R^{26}$, in which $R^{25}$ and $R^{26}$ are identical or different and represent hydrogen, $C_1$-$C_{10}$-alkyl, optionally substituted by one or more halogens, O-alkyl-($C_1$-$C_6$), alkyl ($C_1$-$C_4$) CN, or COO alkyl ($C_1$-$C_6$), hydroxyl, or amino, alkylamino having 1-4 carbon atoms, dialkylamino having 1-3 carbon atoms per alkyl group or phenyl which is optionally substituted by halogen, or represent a group having the formula (II)

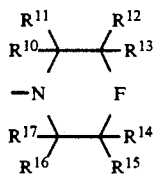

(II)

where

F denotes sulphur, oxygen, nitrogen, $NR^{18}$ or $CR^{19}GR^{20}$ and $R^{18}$ represents hydrogen, methyl, ethyl, propyl, ($C_3$-$C_6$) -cycloalkyl, phenyl, optionally substituted by halogen,

CN,

COO alkyl ($C_1$-$C_4$)

$C_1$-$C_4$-acyl or ($C_1$-$C_4$)-alkyl-sulphonyl, $R^{10}R^{11}$, $R^{17}$ and $R^{16}$ represent hydrogen.

$R^{12}$, $R^{13}$, $R^{14}$, $R^{15}$, $R^{19}$ and $R^{20}$ are identical or different and represent hydrogen, $C_1$-$C_3$ alkyl or $C_3$-C cycloalkyl, optionally substituted by one or more halogens, OH, methoxy, ethoxy, methyl, ethyl, cyano, $CO_2Me$, hydroxyl, or amino, alkylamino having 1-4 carbon atoms or dialkylamino having 1-3 carbon atoms.

$R^3$ and $R^5$ are identical or different and may also represent a group of the formula

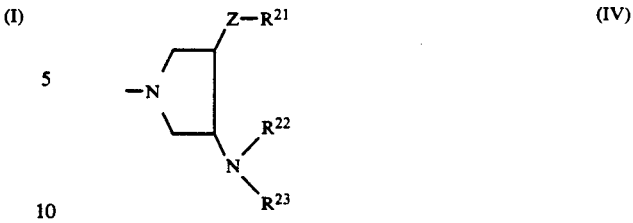

(IV)

where $R^{21}$ can represent hydrogen, methyl, ethyl, phenyl or $C_1$-$C_4$ acyl, $R^{22}$ can represent hydrogen, methyl, ethyl, OH or $OCH_3$ where $R^{21}$ and $R^{22}$ may together also denote a $C_1$-$C_3$-alkylene bridge which is monosubstituted or disubstituted by methyl, $R^{23}$ can represent H, methyl, ethyl, aryl, benzyl, $C_1$-$C_4$-alkoxycarbonyl or $C_1$-$C_4$ acyl, Z can represent O or S, $ZR^{21}$ can represent hydrogen, A represents N or $CR_4$, where $R^4$ represents hydrogen or halogen.

It has furthermore been found that compounds of the formula (I) according to the invention, in which $R^3$ and $R^6$ are identical, are obtained when quinolones of the general formula (III)

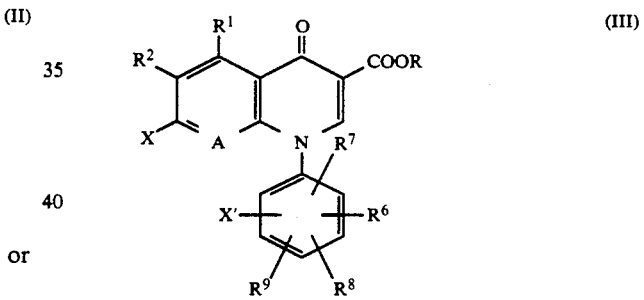

(III)

in which

A, R, $R^1$, $R^2$, $R^4$, $R^6$, $R^7$, $R^8$ and $R^9$ have the above-mentioned meaning and X and X' are identical or different and represent a halogen atom, are reacted with amines of the general formula (IV)

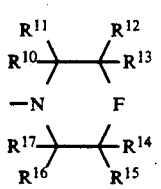

(IV)

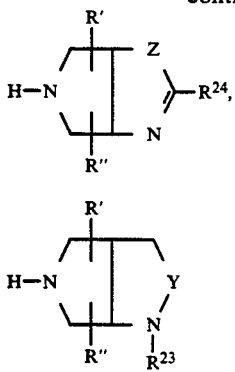

where $R^{10}$–$R^{17}$, F, R', R", R'", Y, Z and $R^{21}$–$R^{24}$ have the above-mentioned meaning.

If, for example, 1-(2,4-difluorophenyl)-6-fluoro-7-chloro-1,4-dihydro-4-oxo-3-quinolinecarboxylic acid and 2-methylpiperazine are used as starting materials, the course of the reaction can be represented by the following equation:

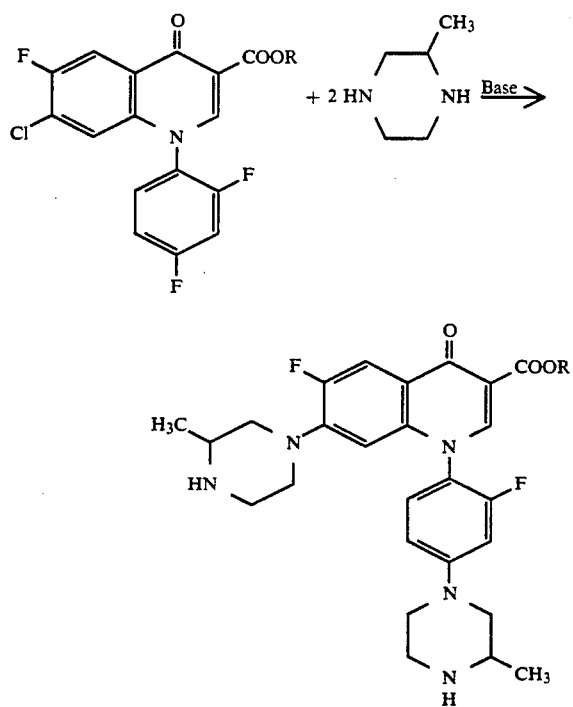

Starting materials of the general formula (III) are known or can be prepared by known processes (European Patent Applications 131,839, 154,780, 302,372 and Belgian Patent Application 904,086).

Examples are:

1-(2,4-difluorophenyl)-6-fluoro-7-chloro-1,4-dihydro-4-oxo-3-quinolinecarboxylic acid,
1-(2,4-difluorophenyl)-6,7-difluoro-1,4-dihydro-4-oxo-3-quinolinecarboxylic acid,
1-(2,4-difluorophenyl)-5,6,7-trifluoro-1,4-dihydro-4-oxo-3-quinolinecarboxylic acid,
1-(2,4-difluorophenyl)-6,7,8-trifluoro-1,4-dihydro-4-oxo-3-quinolinecarboxylic acid,
1-(2,4-difluorophenyl)-6,7-difluoro-8-chloro-1,4-dihydro-4-oxo-3-quinolinecarboxylic acid,
1-(3,4-difluorophenyl)-6,7-difluoro-1,4-dihydro-4-oxo-3-quinolinecarboxylic acid,
1-(2-chloro-4-fluorophenyl)-6,7-difluoro-1,4-dihydro-4-oxo-3-quinolinecarboxylic acid,
1-(3-chloro-4-fluorophenyl)-6,7-difluoro-1,4-dihydro-4-oxo-3-quinolinecarboxylic acid,
ethyl 1-(2,4-difluorophenyl)-6-fluoro-7-chloro-1,4-dihydro-4-oxo-3-quinolinecarboxylate,
ethyl 1-(2,4-difluorophenyl)-6,7-difluoro-1,4-dihydro-4-oxo-3-quinolinecarboxylate,
methyl 1-(2,4-difluorophenyl)-6,7-difluoro-1,4-dihydro-4-oxo-3-quinolinecarboxylate,
7-chloro-6-fluoro-1-(2,4-difluorophenyl)-1,4-dihydro-4-oxo-1,8-naphthyridine-3-carboxylic acid,
1-(2,3,4-trifluorophenyl)-6-fluoro-7-chloro-1,4-dihydro-4-oxo-3-quinolinecarboxylic acid,
1-(2,3,4-trifluorophenyl)-6,7-difluoro-1,4-dihydro-4-oxo-3-quinolinecarboxylic acid,
1-(2,3,4-trifluorophenyl)-6,7,8-trifluoro-1,4-dihydro-4-oxo-3-quinolinecarboxylic acid,
1-(3-nitro-4-fluorophenyl)-6,7-difluoro-1,4-dihydro-4-oxo-3-quinolinecarboxylic acid,
1-(3-nitro-4-fluorophenyl)-6,7,8-trifluoro-1,4-dihydro-4-oxo-3-quinolinecarboxylic acid,
1-(3-nitro-4-fluorophenyl)-6,7-difluoro-8-chloro-1,4-dihydro-4-oxo-3-quinolinecarboxylic acid,
ethyl 7-chloro-6-fluoro-1-(2,4-difluorophenyl)-1,4-dihydro-4-oxo-1,8-naphthyridine-3-quinolinecarboxylate,
1-(4-fluorophenyl)-6-fluoro-7-chloro-1,4-dihydro-4-oxo-3-quinolinecarboxylic acid,
1-(4-fluorophenyl)-6,7-difluoro-1,4-dihydro-4-oxo-3-quinolinecarboxylic acid,
1-(4-fluorophenyl)-6,7-difluoro-8-chloro-1,4-dihydro-4-oxo-3-quinolinecarboxylic acid,
1-(2-fluorophenyl)-6-fluoro-7-chloro-1,4-dihydro-4-oxo-quinolinecarboxylic acid,
1-(2-fluorophenyl)-6,7-difluoro-1,4-dihydro-4-oxo-quinolinecarboxylic acid,
1-(2,4-difluorophenyl)-7-fluoro-1,4-dihydro-4-oxo-quinolinecarboxylic acid,
1-(4-fluorophenyl)-7-fluoro-1,4-dihydro-4-oxo-quinolinecarboxylic acid,
1-(2-fluorophenyl)-7-fluoro-1,4-dihydro-4-oxo-quinolinecarboxylic acid,
7-chloro-6-fluoro-1-(4-fluorophenyl-1,4-dihydro-4-oxo-1,8-naphthyridine-3-carboxylic acid, The amines used according to the invention are known or can be prepared by known methods (Beilsteins Handbuch der Organischen Chemie (Beilstein's Handbook of Organic Chemistry], Volumes 23 and 27, and DE-OS (German Offenlegungsschrift) 3,910,663).

Examples are: piperazine, 1-methylpiperazine, 1-ethylpiperazine, 1-propylpiperazine, 1-isopropylpiperazine, 1-cyclopropylpiperazine, 2-methylpiperazine, 3-ethylpiperazine, 2-cyclohexylpiperazine, 1,2-dimethylpiperazine, 2,2-dimethylpiperazine, 2,8-dimethylpiperazine, 1-(2-hydroxyethyl)-piperazine, 1-phenylpiperazine, morpholine, thiomorpholine, 2-methylmorpholine, 3-methylmorpholine, piperidine, 2-methylpiperidine, 3-methylpiperidine, 4-methylpiperidine, pyrrolidine, 3-(tert.-butoxycarbonylamino)-pyrrolidine, 3-dimethylaminopyrrolidine,
4-amino-3-hydroxypyrrolidine,
3-hydroxy-4-methylaminopyrrolidine,
4-dimethylamino-3-hydroxypyrrolidine,
4-ethylamino-3-hydroxypyrrolidine,
3-amino-4-methoxypyrrolidine,
4-methoxy-3-methylaminopyrrolidine, 3-dimethylamino-4-methoxypyrrolidine,
3-ethylamino-4-methoxypyrrolidine,
3-amino-4-ethoxypyrrolidine,
4-ethoxy-3-methylaminopyrrolidine,
3-dimethylamino-4-ethoxypyrrolidine,
4-ethoxy-3-ethylaminopyrrolidine,
3-hydroxy-4-hydroxyaminopyrrolidine,
3-hydroxy-4-methoxyaminopyrrolidine,
3-hydroxyamino-4-methoxypyrrolidine,
4-methoxy-3-methoxyaminopyrrolidine,
3-benzylamino-4-methoxypyrrolidine,
4-methoxy-3-(5-methyl-2-oxo-1,3-dioxol-4-yl)-methylamino)-pyrrolidine,
3-amino-4-methylmercaptopyrrolidine,
3-acetoxy-4-dimethylaminopyrrolidine,
3-acetoamido-4-methoxypyrrolidine,
4-methoxy-3-methoxycarbonylaminopyrrolidine,
3-formamido-4-methoxypyrrolidine,
3-amino-4-methoxy-2-methylpyrrolidine,
3-amino-4-methoxy-5-methylpyrrolidine,
4-methoxy-2-methyl-3-methylaminopyrrolidine,
4-methoxy-5-methyl-3-methylaminopyrrolidine,
3-amino-4-methoxy-2-phenylpyrrolidine,
4-methoxy-3-methylamino-5-phenylpyrrolidine,
3-methyl-2,7-diazabicyclo(3.3.0)octane,
4-methyl-2,7-diazabicyclo[3.3.0]octane,
5-methyl-2,7-diazabicyclo[3.3.0]octane,
3,5-dimethyl-2,7-diazabicyclo[3.3.0]octane,
1,5-dimethyl-2,7-diazaLbicyclo[3.3.0]octane,
2-oxa-4,7-diazabicyclo[3.3.0]octane,
3,3-dimethyl-2-oxa-4,7-diazaLbicyclo[3.3.0]octane,
3-oxa-2,7-diazabicyclo[3.3.0]octane,
1,2-dimethyl-3-oxa-2,7-diazabicyclo[3.3.0]octane,
2,5-dimethyl-3-oxa-2,7-diazabicyclo[3.3.0]octane,
2,8-dimethyl-3-oxa-2,7-diazabicyclo[3.3.0]octane,
5-methyl-3-oxa-2,7-diazabicyclo(3.3.0)octane,
2-oxa-4,7-diazabicyclo[3.3.0]oct-3-ene,
3-methyl-2-oxa-4,7-diazabicyclo[3.3.0]oct-3-ene,
3-phenyl-2-oxa-4,7-diazabicyclo[3.3.01-3-ene,
6-methyl-2-oxa-4,7-diazabicyclo[3.3.0]oct-3-ene,
8-methyl-2-oxa-4,7-diazabicyclo[3.3.0]oct-3-ene,
3-methyl-2,8-diazabicyclo[4.3.0]nonane,
4-methyl-2,8-diazabicyclo[4.3.0]nonane,
5-methyl-2,8-diazabicyclo[4.3.0]nonane,
6-methyl-2,8-diazabicyclo[4.3.0]nonane,
3-methyl-2-oxa-5,8-diazabicyclo(4.3.0)nonane,
4-methyl-2-oxa-5,8-diazabicyclo(4.3.0)nonane,
1-methyl-2-oxa-5,8-diazabicyclo[4.3.0]nonane,
3,5-dimethyl-2-oxa-5,8-diazabicyclo[4.3.0]nonane,
2-thia-5,8-diazabicyclo(4.3.0)nonane,
5-methyl-2-thia-5,8-diazabicyclo[4.3.0]nonane,
3,5-dimethyl-2-thia-5,8-diazabicyclo[4.3.0]nonane,
3-oxa-2,8-diazabicyclo[4.3.0]nonane,
2-methyl-9-oxa-2,8-diazabicyclo[4.3.0]nonane,
4-methyl-3-oxa-2,8-diazabicyclo[4.3.0]nonane,
2,5-dimethyl-3-oxa-2,8-diazabicyclo(4.3.0)nonane,
3-oxa-5,8-diaza-bicyclo(4.3.0)nonane,
5-methyl-3-oxa-5,8-diazabicyclo[4.3.0]nonane,
1,5-dimethyl-3-oxa-5,8-diazabicyclo[4.3.0]nonane.

The amines can be used as diastereomer mixtures, in diastereomerically pure form, as a racemate or as partially or completely enriched enantiomers.

The reaction of (III) with (IV) according to method A, in which the compounds (IV) can also be employed in the form of their hydrochlorides, is preferably carried out in a diluent such as dimethyl sulphoxide, N,N-dimethylformamide, N-methylpyrrolidone, hexamethylphosphoramide, sulpholane, acetonitrile, water, an alcohol such as methanol, ethanol, n-propanol or isopropanol, glycol monomethylether or pyridine. Mixtures of these diluents may also be used.

Acid binders used can be all customary inorganic and organic acid-binding agents. These preferably include the alkali metal hydroxides, alkali metal carbonates, organic amines and amidines.

The following may be mentioned in particular as particularly suitable: triethylamine, 1,4-diazabicyclo(2.2.2)octane(DABCO) , 1,8-diazabicyclo[5.4.0]undec-7-ene (DBU) or excess amine (IV).

The reaction temperature is kept between 50° C. and 250° C., preferably between 100° C. and 180° C.

The reaction can be carried out at normal pressure, but also at elevated pressure. In general, the reaction is carried out at pressures between 1 and 100 bar, preferably at 1 to 10 bar.

When carrying out the process according to the invention, 2 to 10 mols, preferably 3 to 6 mols, of a compound of the general formula (IV) are employed per mol of a compound of the general formula (III).

The compounds according to the invention are additionally obtained by reacting compounds of the general formula (V)

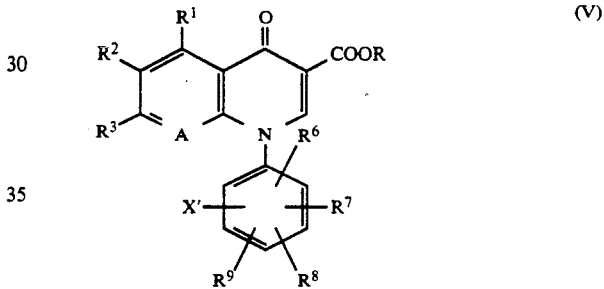

in which A, R and $R^1$ to $R^9$ have the abovementioned meaning and X' represents a halogen atom, with amines of the general formula (IV), if appropriate in the presence of diluents and if appropriate in the presence of acid binders (method B).

If, for example, 1-(2,4-difluorophenyl)-6-fluoro-7-(3-methylpiperazin-1-yl)-1,4-dihydro-4-oxo-3-quinolinecarboxylic acid and 1-methylpiperazine are used as starting materials, the course of the reaction can be represented by the following equation: Equation II:

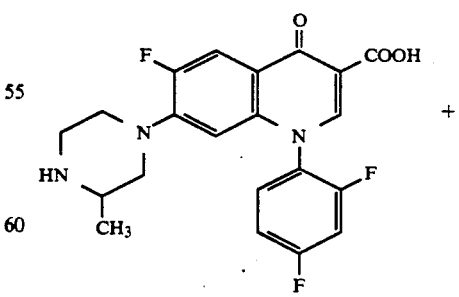

+

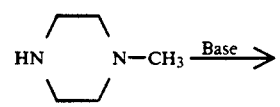

-continued

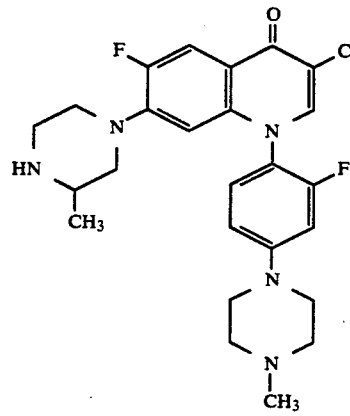

The compounds of the general formula (V) are known or can be prepared by known methods (European Patent Applications 131,839, 154,780 and 302,372). Examples which may be mentioned are:

Compounds of the general formula (V) having the following radicals ($R^7$, $R^8$ and $R^9$ are hydrogen)

| $R^1$ | $R^2$ | $R^3$ | $R^4$ (A = C—$R^4$) | $R^6$ | R | X' |
|---|---|---|---|---|---|---|
| H | F | HN⟨piperazine⟩N— | H | o-F | H | p-F |
| H | F | HN⟨piperazine⟩N— | H | o-F | $C_2H_5$ | p-F |
| H | F | HN⟨3-methylpiperazine⟩N— | H | o-F | H | p-F |
| H | F | HN⟨3-methylpiperazine⟩N— | H | o-F | $C_2H_5$ | p-F |
| H | F | $H_3C$—N⟨piperazine⟩N— | H | m-Cl | H | p-F |
| H | F | $H_3C$—N⟨piperazine⟩N— | H | m-Cl | $C_2H_5$ | p-F |
| H | F | $H_3C$—N⟨piperazine⟩N— | H | o-F | H | p-F |
| H | F | $H_3C$—N⟨piperazine⟩N— | H | o-F | $C_2H_5$ | p-F |
| H | F | $H_3C$—N⟨piperazine⟩N— | H | m-Cl | H | p-F |
| H | F | $H_3C$—N⟨piperazine⟩N— | H | m-Cl | $C_2H_5$ | p-F |

| $R^1$ | $R^2$ | $R^3$ | (A = N) | $R^6$ | R | X' |
|---|---|---|---|---|---|---|
| H | F | HN⟨piperazine⟩N— | | o-F | H | p-F |
| H | F | HN⟨piperazine⟩N— | | o-F | $C_2H_5$ | p-F |
| H | F | $H_3C$—N⟨piperazine⟩N— | | o-F | H | p-F |
| H | F | $H_3C$—N⟨piperazine⟩N— | | o-F | $C_2H_5$ | p-F |
| H | F | HN⟨3-methylpiperazine⟩N— | | o-F | H | p-F |
| H | F | HN⟨3-methylpiperazine⟩N— | | o-F | $C_2H_5$ | p-F |

The compounds according to the invention are additionally obtained when quinolones of the general formula (VI)

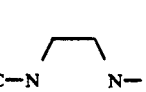

(VI)

in which A, R, $R^1$ to $R^9$ and X have the above-mentioned are reacted with amines of the general formula (IV) if appropriate in the presence of a diluent and if appropriate in the presence of an acid entrainer if, for example 1-[3-chloro-4-(4-methylpiperazinyl)-phenyl]-7-chloro-6-fluoro-1,4-dihydro-4-oxo-3-quinolinecarboxylic acid and 2-methylpiperazine are used as starting materials, the course of the reaction can be represented by the following equation.

Equation II:

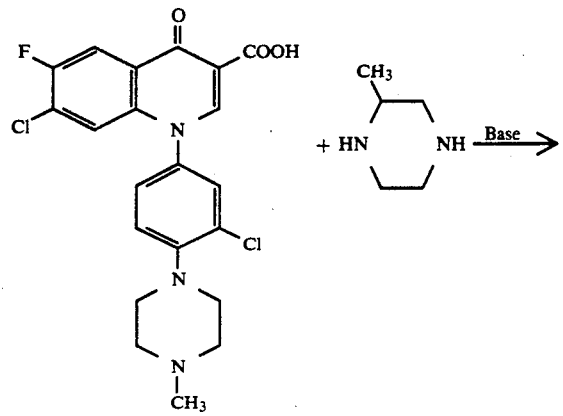

Compounds of the type (VI) are known or can be prepared by known methods. Examples which may be mentioned are:

For $R^1$, $R^2$, $R^6$, $R^7$, $R^8$ and $R^9$ equal to hydrogen

| X | $R^4$ (A = $CR^4$) | $R^5$ | R |
|---|---|---|---|
| F | H | 4-N⌒NMe (piperazine) | $C_2H_5$ |
| F | H | 4-N⌒O (morpholine) | $CH_3$ |
| F | H | 4-N-pyrrolidine-NMe$_2$ | $CH_3$ |

-continued

| X | $R^4$ (A = $CR^4$) | $R^5$ | R |
|---|---|---|---|
| F | H | 4-N⌒NMe | H |
| F | H | 4-N⌒O | H |
| F | H | 4-N-pyrrolidine-NMe$_2$ | H |
| F | H | 4-N⌒NH, Me | $C_2H_5$ |
| F | H | 4-N⌒NH, Me | H |

For $R^1$, $R^2$, $R^7$, $R^8$, $R^9$ equal to hydrogen

| X | $R^4$ (A = $C-R^4$) | $R^5$ | $R^6$ | R |
|---|---|---|---|---|
| F | H | 4-N⌒NMe | 3-Cl | H |
| F | H | 4-N⌒O | 3-Cl | $C_2H_5$ |
| F | H | 4-N⌒NMe, Me | 3-Cl | H |
| F | H | 4-N⌒NMe | 3-$CF_3$ | H |
| F | H | 4-N⌒NMe, Me | 3-$CF_3$ | H |
| F | H | 2-N⌒NMe | 4-$CH_3$ | H |

-continued
| X | R⁴ (A = C—R⁴) | R⁵ | R⁶ | R |
|---|---|---|---|---|
| F | H |  2-N⟩O | 4-CH₃ | C₂H₅ |
| F | H |  3-N⟩NMe | 5-CH₃ | H |
| F | H |  3-N⟩O | 5-CH₃ | H |
| F | H |  3-N⟩O | H | H |
For R¹=H, R²=F, R⁶-R⁹=H
| X | R⁴ (A = CR⁴) | R⁵ | R |
|---|---|---|---|
| F | H | 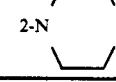 2-N⟩O | H |
| X | R⁴ | R⁵ | R |
|---|---|---|---|
| F | H | 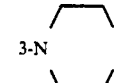 3-N⟩O | H |
| F | H | 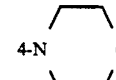 4-N⟩O | C₂H₅ |
| F | H | 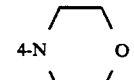 4-N⟩O | H |
| F | H | 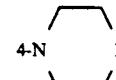 4-N⟩NMe | H |
| F | H | 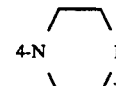 4-N⟩NMe | C₂H₅ |
| F | H | 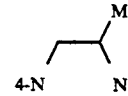 4-N⟩NMe (Me) | H |
| F | H | 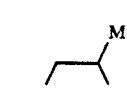 4-N⟩NH (Me) | H |
-continued
| X | R⁴ | R⁵ | R |
|---|---|---|---|
| F | Cl |  2-N⟩O | H |
| F | Cl |  3-N⟩O | H |
| F | Cl |  4-N⟩O | H |
| F | Cl |  4-N⟩NMe | H |
| F | Cl | 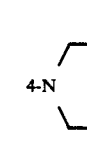 4-N⟩NH (Me) | H |
| F | Cl |  4-N⟩NMe (Me) | H |
| F | Cl |  4-N⟩NMe | C₂H₅ |
| F | Cl |  4-N⟩O | CH₃ |
| F | H |  4-N⟩NMe₂ | H |
| F | H |  4-N⟩NMe₂ | C₂H₅ |
| F | H |  4-N⟩O (CH₃) | H |
| F | H |  4-N⟩NMe | H |

R₁=H, R₂=F, X=F, R⁴=H (A=CR⁴), R⁷=H, R⁸=H, R⁹=H

| R⁵ | R⁶ | R |
|---|---|---|
| 4-N(piperazine)NMe | 3-Cl | H |
| 4-N(piperazine)NMe | 3-Cl | C₂H₅ |
| 4-N(morpholine)O | 3-Cl | H |
| 4-N(pyrrolidine)-3-NMe₂ | 3-Cl | H |
| 4-N(piperidine) 2-Me, NMe | 3-Cl | H |
| 4-N(piperazine)NMe | 3-CF₃ | H |
| 4-N(morpholine)O | 3-CF₃ | H |
| 4-N(piperazine)NMe | 3-CH₃ | H |
| 4-N(piperazine) 2-Me, NH | 3-CH₃ | H |
| 2-N(piperazine)NMe | 4-CH₃ | H |
| 2-N(morpholine)O | 4-CH₃ | H |
| 4-N(piperazine)NMe | 2-OCH₃ | H |
| 4-N(piperazine) 2-Me, NH | 2-OCH₃ | H |
| 4-N(morpholine)O | 2-OCH₃ | C₂H₅ |
| 3-N(piperazine)NCH₃ | 2-CH₃ | H |
| 3-N(piperazine)NH | 2-CH₃ | H |
| 4-N(piperazine)NMe | 3-CN | H |
| 5-N(piperazine)NCH₃ | 2-NO₂ | H |
| 5-N(morpholine)O | 2-NO₂ | H |
| 4-N(piperazine)NCH₃ | 3-NHCOCH₃ | H |
| 4-N(piperazine) 2-CH₃, NH | 3-NHCOCH₃ | H |
| 4-N(piperazine)NCH₃ | 2-F | H |
| 4-N(piperidine) 2-CH₃, NH | 2-F | H |
| 4-N(morpholine)O | 2-F | H |

-continued

| R⁵ | R⁶ | R |
|---|---|---|
| 4-cyclohexyl-NMe₂ | 2-F | H |
| 5-N-piperazine-NCH₃ | 2-NO₂ | H |
| 5-N-morpholine-O | 2-NO₂ | H |
| 5-N-piperazine-NCH₃ | 2-NH₂ | H |
| 5-N-piperazine-NCH₃ | 3-NH₂ | H |
| 4-N-morpholine-O | 3-NH₂ | H |
| 4-N-cyclohexyl-NMe₂ | 3-NH₂ | H |
| 4-N-piperazine-NCH₃ | 3-NO₂ | H |
| 4-N-morpholine-O | 3-NO₂ | H |
| 4-N-piperazine(CH₃)-NH | 3-NH₂ | H |
| 4-N-piperazine-NCH₃ | 3-NH₂ | H |
| 4-N-piperazine-NCH₃ | 2-F | 3F(R⁷) H |

-continued

| R⁵ | R⁶ | R |
|---|---|---|
| 4-N-piperazine-NCH₃ | 2F | 6F(R⁷) H |

R₁=H, R₂=F, X=F, R⁴=Cl (A=CR₄), R⁷=H, R⁸=H, R⁹=H

| R⁵ | R⁶ | R |
|---|---|---|
| 4-N-piperazine-NMe | 3-Cl | H |
| 4-N-piperazine-NMe | 3-Cl | C₂H₅ |
| 4-N-morpholine-O | 3-Cl | H |
| 4-N-piperazine-NMe | 3-CF₃ | H |
| 4-N-morpholine-O | 3-CH₃ | H |
| 2-N-piperazine-NCH₃ | 4-CH₃ | H |
| 4-N-piperazine-NMe | 2-OCH₃ | H |
| 4-N-piperazine-NMe | 2-CH₃ | H |
| 4-N-piperazine-NMe | 3-CN | H |
| 4-N-piperazine(CH₃)-H | 3-CN | H |
| 5-N-piperazine-NCH₃ | 2-NO₂ | H |

| R[5] | R[6] | R |
|---|---|---|
| 5-N(morpholino) | 2-NO$_2$ | H |
| 5-N(morpholino) | 2-NO$_2$ | C$_2$H$_5$ |
| 4-N(N-methylpiperazinyl) | 3-NHCOCH$_3$ | H |
| 4-N(3-methylpiperazinyl) | 3-NHCOCH$_3$ | H |
| 4-N(N-methylpiperazinyl) | 2-F | H |
| 4-N(morpholino) | 2-F | H |
| 4-N(2-methylpiperazinyl) | 2-F | H |
| 4-N(3-dimethylaminopyrrolidinyl) | 2-F | H |
| 4-N(N-methylpiperazinyl) | 3-NH$_2$ | H |
| 4-N(morpholino) | 3-NH$_2$ | H |
| 4-N(3-methylpiperazinyl) | 3-NH$_2$ | H |
| 4-N(N-methylpiperazinyl) | 3-NO$_2$ | H |
| 4-N(3-methylpiperazinyl) | 3-NO$_2$ | H |

$R_1=F$, $R_2=F$, $X=F$, $R^4=F$ (A=CR$_4$), $R^7=H$, $R^8=H$, $R^9=H$

| R[5] | R[6] | R |
|---|---|---|
| 4-N(4-methylpiperazinyl, NMe) | 3-Cl | C$_2$H$_5$ |
| 4-N(4-methylpiperazinyl, NMe) | 3-CF$_3$ | H |
| 4-N(morpholino) | H | H |
| 4-N(3-methylpiperazinyl) | H | H |
| 4-N(3-dimethylaminopyrrolidinyl) | H | H |
| 4-N(N-methylpiperazinyl) | 2-F | C$_2$H$_5$ |
| 4-N(N-methylpiperazinyl) | 2-F | H |
| 4-N(morpholino) | 2-F | H |
| 4-N(3-methylpiperazinyl) | 2-F | H |
| 4-N(3-dimethylaminopyrrolidinyl) | 2-F | H |

-continued

| R⁵ | R⁶ | R |
|---|---|---|
| 4-N⌬NCH₃ | 3-F | H |
| 4-N⌬NCH₃ | 2-CH₃ | H |
| 4-N⌬NCH₃ | 3-CH₃ | H |
| 4-N⌬NCH₃ | 3-CF₃ | H |
| 4-N⌬NCH₃ | 3-NHCOCH₃ | H |
| 4-N⌬NH (CH₃) | 3-NHCOCH₃ | H |
| 4-N⌬NCH₃ | 3-NH₂ | H |
| 4-N⌬O | 3-NH₂ | H |
| 4-N⌬NH (CH₃) | 3-NH₂ | H |
| 4-N⌬NCH₃ | 3-NO₂ | H |
| 4-N⌬NCH₃ | 3-CN | H |
| 4-N⌬NCH₃ | 2-NH₂ | H |
| 2-N⌬NCH₃ | H | H |

$R^1=H$, $R^2=NO_2$, $X=F$, $R^4=H$ (A=CR⁴), $R^7=H$, $R^8=H$, $R^9=H$

| R⁵ | R⁶ | R |
|---|---|---|
| 4-N⌬NMe | H | C₂H₅ |
| 4-N⌬NMe | 3-Cl | H |
| 4-N⌬O | H | H |
| 2-N⌬O | H | H |
| 3-N⌬O | H | H |
| 4-N⌬NCH₃ | 2-F | C₂H₅ |
| 4-N⌬NH | 2-F | H |
| 4-N⌬O | 2-F | H |
| 4-N⌬NH (CH₃) | 2-F | H |
| 4-N⌬(NMe₂) | 2-F | H |

$R^1=H$, $R^2=F$, $X=F$, $R^4=H$ (A=CR⁴)

| R⁵ | R⁶ | R⁷ | R⁸ | R⁹ | R |
|---|---|---|---|---|---|
| 4-N⌬NMe | F | F | F | F | C₂H₅ |

-continued

| R⁵ | R⁶ | R⁷ | R⁸ | R⁹ | R |
|---|---|---|---|---|---|
| 4-N(piperazinyl)NMe | F | F | F | F | H |
| 4-N(morpholinyl)O | F | F | F | F | H |
| 4-N(2-methylpiperazinyl)NH, CH₃ | F | F | F | F | H |
| 4-N(piperazinyl)NH | F | F | F | F | H |
| 4-N(3-dimethylaminopyrrolidinyl)NMe₂ | F | F | F | F | H |
| 4-N(piperazinyl)NMe | 2-F | 3-F | H | H | H |
| 4-N(morpholinyl)O | 2-F | 3-F | H | H | H |
| 4-N(piperazinyl)NH | 2-F | 3-F | H | H | H |
| 4-N(2-methylpiperazinyl)NH, CH₃ | 2-F | 3-F | H | H | H |
| 4-N(3-dimethylaminopyrrolidinyl)NMe₂ | 2-F | 3-F | H | H | H |
| 4-N(piperazinyl)NMe | 2-F | 6-F | H | H | H |
| 4-N(piperazinyl)NH | 2-F | 6-F | H | H | H |
| 4-N(3-methylpiperazinyl)NH, Me | 2-F | 6-F | H | H | H |

-continued

| R⁵ | R⁶ | R⁷ | R⁸ | R⁹ | R |
|---|---|---|---|---|---|
| 4-N(piperazinyl)NH | 2-F | 6-F | H | H | H |

R¹=H, R²=F, X=F, A=N,

| R⁵ | R⁶ | R⁷ | R⁸ | R⁹ | R |
|---|---|---|---|---|---|
| 4-N(piperazinyl)NCH₃ | H | H | H | H | Et |
| 4-N(piperazinyl)NCH₃ | H | H | H | H | H |
| 4-N(morpholinyl)O | H | H | H | H | H |
| 4-N(3-dimethylaminopyrrolidinyl)NMe₂ | H | H | H | H | H |
| 4-N(2-methylpiperazinyl)NH, CH₃ | H | H | H | H | H |
| 2-N(piperazinyl)NCH₃ | H | H | H | H | H |
| 4-N(piperazinyl)NCH₃ | H | H | 2-F | 3-F | H |
| 4-N(2-methylpiperazinyl)NH, CH₃ | H | H | 2-F | 3-F | H |
| 4-N(piperazinyl)NCH₃ | H | H | 2-F | 6-F | H |
| 4-N(piperazinyl)NCH₃ | F | F | F | F | H |
| 4-N(piperazinyl)NCH₃ | H | H | H | 2-F | H |

| $R^5$ | $R^6$ | $R^7$ | $R^8$ | $R^9$ | R |
|---|---|---|---|---|---|
| 4-N(piperazinyl)NCH3 | H | H | H | 2-CH3 | H |
| 4-N(piperazinyl)NCH3 | H | H | H | 3-CF2 | H |
| 4-N(piperazinyl)NCH3 | H | H | H | 3-NO2 | H |
| 4-N(piperazinyl)NCH3 | H | H | H | 3-NHCOCH3 | H |
| 4-N(piperazinyl)NCH3 | H | H | H | 3-NH2 | H |
| 4-N(piperazinyl)NCH3 | H | H | H | 3-Cl | H |
| 4-N(piperazinyl with CH3)NH | H | H | H | 3-Cl | H |
| 4-N(morpholino)O | H | H | H | 3-Cl | H |
| 2-N(piperazinyl)NCH3 | H | H | H | H | H |
| 3-N(piperazinyl)NCH3 | H | H | H | H | H |
| 4-N(piperazinyl with CH3)NH | H | H | 2-F | 3-F | H |

$R^1$=H, $R^2$=F, X=F, $R^4$=Cl (A=CR$^4$)

| $R^5$ | $R^6$ | $R^7$ | $R^8$ | $R^9$ | R |
|---|---|---|---|---|---|
| 4-N(piperazinyl)NMe | F | F | F | F | H |
| 4-N(piperazinyl)NH | F | F | F | F | H |
| 4-N(piperazinyl with CH3)NH | F | F | F | F | H |
| 4-N(morpholino)O | F | F | F | F | H |
| 4-N(piperazinyl)NCH3 | 2-F | 3-F | H | H | H |
| 4-N(pyrrolidinyl with NMe2) | 2-F | 3-F | H | H | H |
| 4-N(morpholino)O | 2-F | 3-F | H | H | H |
| 4-N(piperazinyl)NCH3 | 2-F | 6-F | H | H | H |
| 4-N(piperazinyl with CH3)NH | 2-F | 6-F | H | H | H |

Some of the compounds according to the invention are obtained by starting from compounds of the general formula

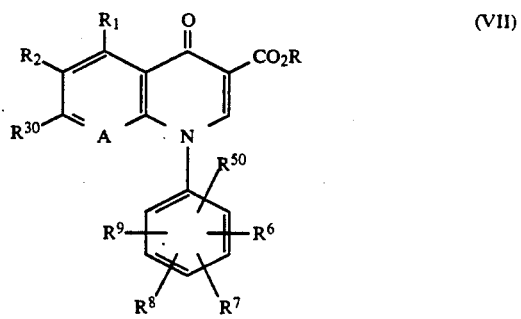

(VII)

where R, $R^1$, $R^2$, A and $R^6$–$R^9$ have the abovementioned meaning and the radicals $R^{30}$ and $R^{50}$ are identical or different.

The general formula (VII) is distinguished by the fact that secondary or primary amines are present in $R^{30}$ and in $R^{50}$, only in $R^{30}$ or only in $R^{50}$. The structures of $R^{30}$ and $R^{50}$ are determined by the substituents of the above-defined radicals $R^3$ or $R^5$, to which this criterion applies.

These compounds are reacted with acylating agents or alkylating agents of the general formula (VIII)

$$V-W \qquad (VIII)$$

in which W=

CN $(C_2-C_4)$-acyl, optionally substituted $(C_1-C_4)$ -sulphonyl $(C_1-C_4)$ -alkoxycarbonyl $(C_1-C_5)$-alkyl and V represents a leaving group, such as

V= halogen trifluoromethanesulphonate mesylate tosylate acetate trihaloacetate if appropriate in the presence of diluents and if appropriate in the presence of acid binders (method D).

If, for example, 1-(2-fluoro-4-piperazinylphenyl)-6-fluoro-7-piperazinyl-1,4-dihydro-4-oxo-3-quinolinecarboxylic acid and methanesulphonyl chloride are used as starting materials, the course of the reaction can be represented by the following equation.

Equation IV:

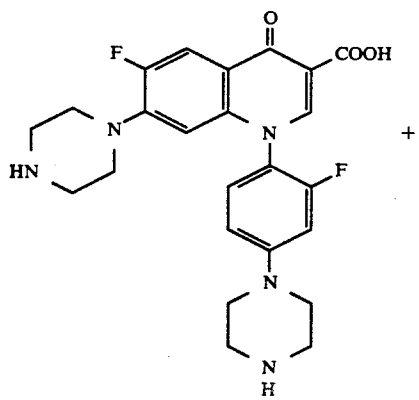

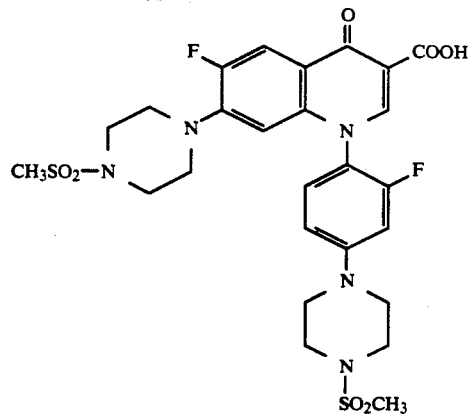

Compounds of the type (VII) can be prepared by the methods A, B and C.

Compounds of the type (VIII) are known (Beilsteins Handbuch der Organischen Chemie [Beilstein's Handbook of Organic Chemistry], volumes 2 and 3). Examples which may be mentioned are: cyanogen bromide, acetyl chloride, propionyl chloride, butyryl chloride and methanesulphonyl chloride. The corresponding anhydrides (for example acetic anhydride) can also be used instead of organic acid chlorides.

Diluents employed in the reaction of (VII) with (VIII) are preferably dimethyl sulphoxide, N,N-dimethylformamide, acetonitrile, pyridine or mixtures of these diluents. Acid binders which can be used are all customary inorganic and organic acid-binding agents. These preferably include the alkali metal hydroxides, alkali metal carbonates, organic amines and amidines. The following may be mentioned in detail as particularly suitable: triethylamine, 1,4-diazabicyclo(2.2.2)octane, (DABCO) and 1,8-diazaLbicyclo[5.4.0]undec-7-ene, (DBU).

The reaction is carried out in the temperature range between $-100°$ C. and $200°$ C., preferably between $-20°$ C. and $100°$ C.

The reaction can be carried out at normal pressure, but also at elevated pressure. In general, the reaction is carried out at pressures between 1 and 100 bar, preferably at 1 to 10 bar.

When carrying out the process according to the invention, 1 to 10 mols, preferably 2 to 6 mols of a compound of the general formula (VIII) are in general employed per mol of a compound of the general formula (VII).

Other compounds according to the invention are obtained when compounds of the general formula (VII) are reacted with compounds of the general formula (IX)

$$CH_2=CH-U \qquad (IX)$$

in which U denotes an electron-attracting group such as COOB, COB, $CONH_2$, CN, $SO_2B$ or $SO_3B$ and B represents $C_1-C_4$-alkyl which is optionally substituted, if appropriate in the presence of diluents (method E)

If, for example, 1-(2-fluoro-4-piperazinylphenyl)-6-fluoro-7-piperazinyl-1,4-dihydro-4-oxo-3-quinolinecarboxylic acid and ethyl acrylate are used as starting materials, the course of the reaction can be represented by the following equation (V):

Equation V:

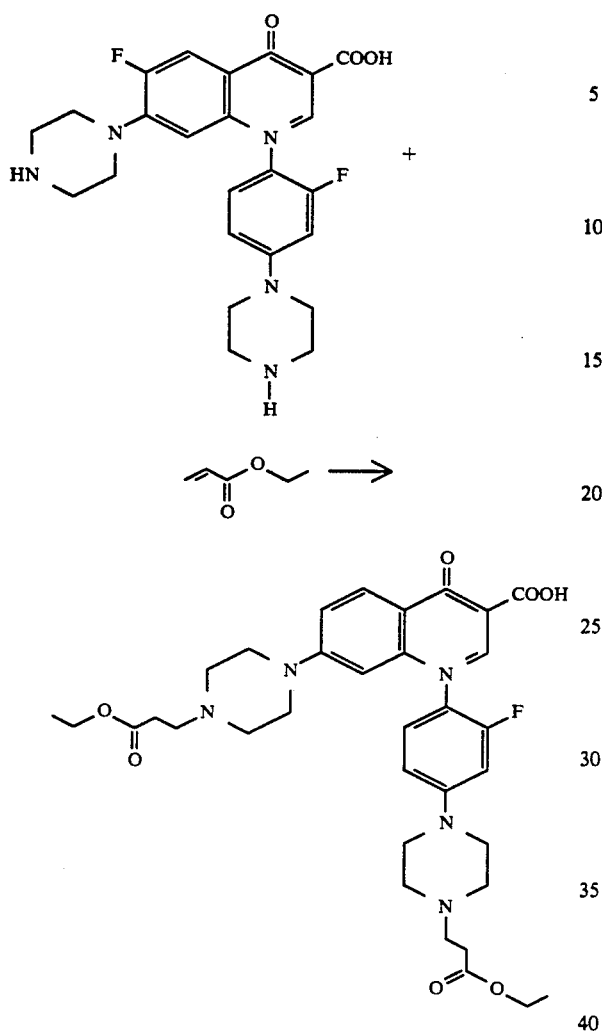

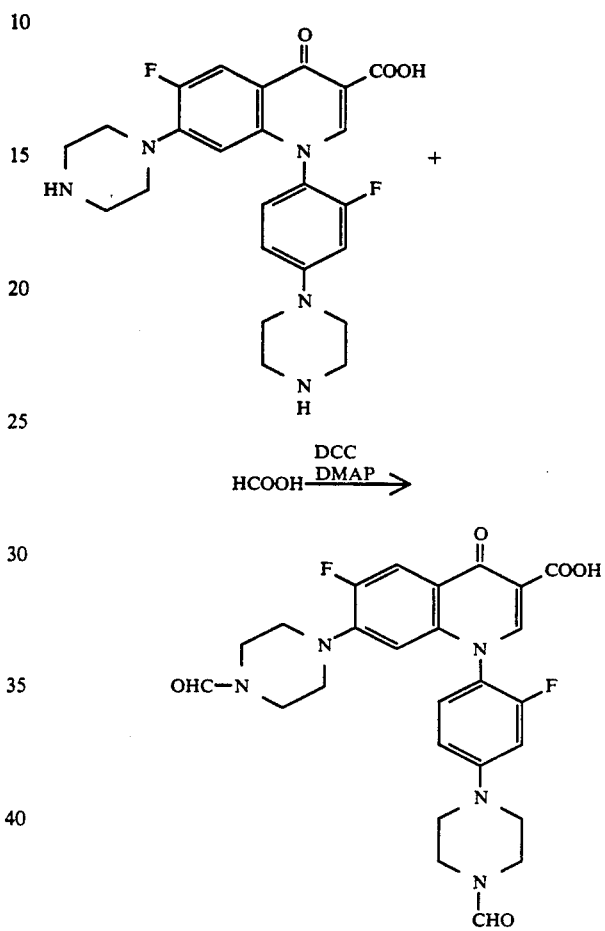

The reaction of (VII) with (IX) according to method E is preferably carried out in a diluent such as dimethyl sulphoxide, N,N-dimethylformamide, sulpholane, acetonitrile, water, an alcohol such as methanol, ethanol, n-propanol or isopropanol, glycol monomethylether or pyridine. Mixtures of these diluents may also be used.

The reaction temperature is in the range between −100° C. and 200° C., preferably between −20° C. and 80° C.

The reaction can be carried out at normal pressure, but also at elevated pressure. In general, the reaction is carried out at pressures between 1 and 100 bar, preferably at 1 to 10 bar.

When carrying out the process according to the invention, 1 to 10 mols, preferably 2 to 6 mols of a compound of the general formula (IX) are employed per mol of a compound of the general formula (VII).

Compounds according to the invention are also obtained when compounds of the general formula (VII) are reacted with carboxylic acids of the general formula (X)

D—COOH        (X)

in which D represents H or optionally substituted ($C_1$–$C_4$)-alkyl, if appropriate in the presence of diluents and if appropriate in the presence of dehydrating reagents and if appropriate in the presence of a catalyst (method F)

If, for example, 1-(2-fluoro-4-piperazinylphenyl)-6-fluoro-7-piperazinyl-1,4-dihydro-4-oxo-3-quinolinecarboxylic acid and formic acid are used as starting materials, the course of the reaction can be represented by the following equation (VI).

Equation VI:

The reaction can be carried out at normal pressure, but also at elevated pressure. In general, the reaction is carried out at pressures between 1 and 100 bar, preferably at 1 to 10 bar.

When carrying out the process according to the invention, 1 to 10 mols, preferably 2 to 6 mols of a compound of the general formula (X) are employed per mol of a compound of the general formula (VII).

Compounds of the type (X) are known (Beilstein, volumes 2 and 3). Examples which may be mentioned are: formic acid, acetic acid, propionic acid and isobutyric acid.

The reaction of (VII) to give (X) is preferably carried out in a diluent such as dimethyl sulphoxide, N,N-dimethylformamide, N-methylpyrrolidone, hexamethylphosphoramide, sulpholane, acetonitrile, methylene chloride, benzine, toluene or pyridine. Mixtures of these diluents may also be used.

Suitable dehydrating agents are preferably molecular sieve, solvents such as methylene chloride, benzene or toluene, which form azeotropes with water, but are immiscible with water, or compounds which react with water but not with the reaction components, such as, for example, dicyclohexylcarbodiimide (DCC). 4-N,N-Dimethylaminopyridine (DMAP), for example, can be used as a catalyst.

The reaction temperature is in the range from −100° C. to 200° C., preferably in the range from 0° C. to 150° C.

The acid addition salts of the compounds according to the invention are prepared in a customary manner, for example by dissolving the betaine in excess aqueous acid and precipitating the salts using a water-miscible organic solvent such as methanol, ethanol, acetone or acetonitrile. Equivalent amounts of betaine and acid can also be heated in water or an alcohol such as glycol monomethyl ether and then evaporated to dryness or the precipitated salt filtered off with suction. Pharmaceutically utilizable salts are to be understood as meaning, for example, the salts of hydrochloric acid, sulphuric acid, acetic acid, glycolic acid, lactic acid, succinic acid, citric acid, tartaric acid, methanesulphonic acid, galacturonic acid, gluconic acid, embonic acid, glutamic acid or aspartic acid.

The alkali metal or alkaline earth metal salts of the carboxylic acids according to the invention are obtained, for example, by dissolving the betaine in a subequivalent amount of alkali metal hydroxide or alkaline earth metal hydroxide solution, filtering off undissolved betaine and evaporating the filtrate to dryness. Sodium salts, potassium salts or calcium salts are pharmaceutically suitable . The corresponding silver salts are obtained by reaction of an alkali metal salt or an alkaline earth metal salt with a suitable silver salt such as silver nitrate.

The compounds shown in Table 1 as examples can also be prepared in addition to the active compounds mentioned in the examples, it being possible for these compounds to be present both as diastereomer mixtures and as diastereomerically pure or enantiomerically pure compounds.

TABLE 1

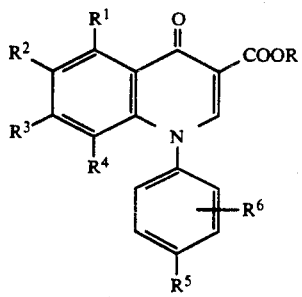

$A = CR^4$

| $R^1$ | $R^2$ | $R^3$ | $R^4$ | $R^6$ | $R^5$ | R | $^1$H-NMR (LM) or MS or m.p. |
|---|---|---|---|---|---|---|---|
| H | F | (2-methyl-piperidinyl-CH$_2$) | H | o-F | as $R^3$, 4-position | H | (CDCL$_3$); 0,90(T, 3H) 1,03(T, 3H), 1,51(Q, 4H), 2,4–3,7(M, 14H), 6,40 (D, 1H)6,78(M, 2H), 7,21 (T, 1H), 8,04(D, 1H), 8,60(S, 1H) |
| | | (3-C$_8$H$_{17}$-piperazinyl-CH$_2$) | " | " | " | " | |
| | | (3-cyclohexyl-piperazinyl-CH$_2$) | " | " | " | " | |
| | | (3-phenyl-piperazinyl-CH$_2$) | " | " | " | " | |

TABLE 1-continued

| | | R group | | R3 | | | Notes |
|---|---|---|---|---|---|---|---|
| | | piperazine-N-CH3 | " | " | " | " | MS: 525(M+), 481, 466, 397, 84(100%), 70, 57, 42 |
| H | F | piperazine-N-C3H7 | H | o-F | as R3, 4-position | | m.p. 180° C. |
| | | piperazine-N-C4H9 | " | " | " | " | |
| | | piperazine-N-CH(CH3)2 | " | " | " | " | m.p.: decomposition from 280° C. |
| | | piperazine-N-cyclopentyl | " | " | " | " | MS: 549(M+), 520(100%) 476, 453, 398, 379, 233, 96, 68, 42 |
| | | piperazine-N-cyclopropyl | " | " | " | " | m.p. 170° C. |
| | | piperazine-N-CH2CH(CH3)2 | " | " | " | " | |
| | | piperazine-N-propyl | " | " | " | " | m.p. 203° C. |
| | | piperazine-N-CH2CH2OH | " | " | " | " | (CF3COOD)3,60(M, 12H), 4,1(M, 8H), 4,3(M, 4H), 6,97(D, 1H), 7,10(M, 2H) 7,63(T, 1H), 8,40(D, 1H), 9,20(S, 1H) |
| | | piperazine with C(CH3)2-NH | " | " | " | " | m.p.: decomposition from 240° C. |
| | | piperazine with CH(CH3)-N-CH3 | " | " | " | " | |
| H | F | pyrrolidine-NHBoc | H | o-F | as R3 | H | m.p.: decomposition from 210° C. |
| | | pyrrolidine-NH2 | | | 4-position | | |

TABLE 1-continued
| | | | | | |
|---|---|---|---|---|---|
| | 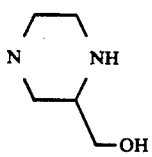 | " " | " | " | m.p.: decomposition from 240° C. |
| | 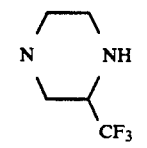 | " " | " | " | |
| | 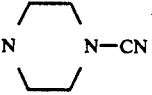 | " " | " | " | (CF$_3$COOD); 3,6–4,4(M, 16H), 6,60(D, 1H), 7,95(M, 2H), 8,07(T, 1H), 8,33(D, 1H), 9,20(S, 1H); m.p. 210° C. |
| | 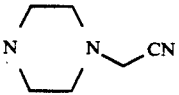 | " ". | " | " | m.p. 200° C. |
| | 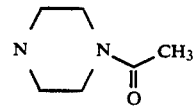 | " " | " | " | m.p. 152° C. |
| | 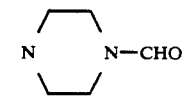 | " " | " | " | m.p. 200° C. |
| H F |  | F o-F | as R$^3$, 4-position | H | |
| | 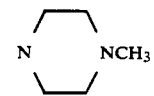 | " " | " | " | (CD$_3$OD); 2,37(S, 3H), 2,40(S, 3H), 2,61(T, 4H), 2,69(T, 4H), 3,3 under LM), 3,40(T, 4H), 6,90(M, 2H), 7,43(T, 1H), 7,94(D, 1H), 8,54(S,1H) |
| | 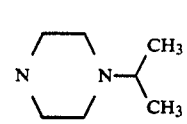 | " " | " | " | |
| | 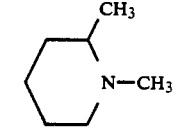 | " " | " | " | |
| | 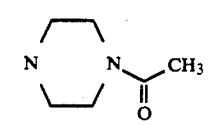 | " " | " | " | |
| | 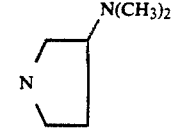 | " " | " | " | |

TABLE 1-continued

| | | | | | | |
|---|---|---|---|---|---|---|
| | | N-piperazinyl-N'-ethyl | " | " | " | " |
| H | F | 2-methylpiperazinyl-NH | H | n-Cl | 4-N-piperazinyl-N-CH₃ | H |
| | | N-piperazinyl-N-isopropyl | " | " | " | " |
| | | 2-methyl-N-piperazinyl-N-acetyl | " | " | " | " |
| | | 2-methyl-N-piperazinyl-N-CH₃ | " | " | " | " |
| | | N-piperazinyl-N-ethyl | " | " | " | " |
| | | 3-(dimethylamino)pyrrolidinyl | " | " | " | " |
| | | N-piperazinyl-N-CH₃ | " | " | " | " (CF₃COOD); 3,16(S, 3H), 3,20 (S, 3H), 3,4–4,1(M, 16H), 6,98 (D, 1H), 7,56(D, 1H), 7,63 (D, 1H), 7,80(D, 1H), 8,40 (D, 1H), 9,22(S, 1H) |
| H | F | 3-methylpiperazinyl-NH | H | o-F | 4-N-piperazinyl-N-CH₃ | H |
| " | " | " | " | " | 4-N-piperazinyl-N-ethyl | |
| " | " | " | " | " | 4-N-piperazinyl-NH | |
| " | " | " | " | " | 3-methyl-4-N-piperazinyl-N-CH₃ | |

TABLE 1-continued

| | | | | | | |
|---|---|---|---|---|---|---|
| H | F | N–N–CH₃ (piperazine, N-methyl) | H | o-F | 4-N–NH (piperazine) | H |
| " | " | " | " | " | 4-N–N–C(O)CH₃ with CH₃ branch (N-acetyl-methylpiperazine) | |
| " | " | " | " | " | 4-N–N–CH₃ with CH₃ branch (dimethylpiperazine) | |
| F | F | N–N–CH₃ (piperazine, N-methyl) | H | o-F | as R³, 4-position | H |
| | | CH₃-branched N–NH (piperazine) | " | " | " | " |
| | | CH₃-branched N–N–CH₃ (piperazine) | " | " | " | " |
| | | CH₃-branched N–N–C(O)CH₃ (piperazine) | " | " | " | " |
| | | N(CH₃)₂-substituted pyrrolidine | " | " | " | " |
| | | morpholine (N–O) | " | " | " | " |
| H | F | N–N–CH₃ (piperazine, N-methyl) | F | o-F | as R³, 4-position | H |
| | | CH₃-branched piperidine N–CH₃ | " | " | " | " |
| | | N–N–C(O)CH₃ (N-acetylpiperazine) | " | " | " | " |

TABLE 1-continued

| | | | | | | | |
|---|---|---|---|---|---|---|---|
| H | F | 3-(N(CH₃)₂)-pyrrolidinyl | F | o-F | as R³, 4-position | H | |
| | | morpholino | " | " | " | " | |
| H | Cl | 4-methylpiperazinyl | H | o-F | as R³, 4-position | H | |
| | | 3-methylpiperazinyl (NH) | " | " | " | " | |
| | | 3-methyl-4-methylpiperazinyl | " | " | " | " | |
| | | 3-methyl-4-acetylpiperazinyl | " | " | " | " | |
| | | 3-(N(CH₃)₂)-pyrrolidinyl | " | " | " | " | |
| | | morpholino | " | " | " | " | |
| H | Cl | 4-methylpiperazinyl | H | o-F | = R³, 4-position | C₂H₅ | |
| F | F | | H | " | " | " | |
| H | F | | F | " | " | " | |
| H | Cl | | H | m-Cl | " | " | |
| H | F | | H | " | " | " | |
| F | F | | H | " | " | " | |
| H | F | | Cl | o-F | " | " | |
| H | F | 4-methylpiperazinyl | Cl | o-F | = R³, 4-position | H | |
| | | morpholino | " | " | " | " | |

TABLE 1-continued

| | | | |
|---|---|---|---|
| 3-methylpiperazinyl (CH₃ on ring, NH) | " " | " | " |
| 2-methyl-4-acetylpiperazinyl | " " | " | " |
| 3-(dimethylamino)pyrrolidinyl | " " | " | " |

| R¹ | R² | R³ | R⁴ | R⁵ | R⁶ | R | ¹H-NMR (LM) or MS or m.p. |
|----|----|----|----|----|----|---|---------------------------|
| H | H | —N(CH₂CH₂)₂NMe (4-methylpiperazin-1-yl) | H | 4-N(CH₂CH₂)₂O (morpholin-4-yl) | H | C₂H₅ | |
| H | H | —N(CH₂CH₂)₂NMe | H | 3-N(CH₂CH₂)₂O | H | H | |
| H | H | —N(CH₂CH₂)₂NMe | H | 2-N(CH₂CH₂)₂O | H | H | |
| H | H | —N(CH₂CH₂)₂NMe | H | 4-N(CH₂CH₂)₂NMe | H | H | |
| H | H | 3-methylpiperazin-1-yl | H | 4-(3-methylpiperazin-1-yl) | H | H | |
| H | H | 2-methyl-4-methylpiperazin-1-yl | H | 4-N(CH₂CH₂)₂NMe | H | H | |
| H | H | 3-(dimethylamino)pyrrolidin-1-yl | H | 4-N(CH₂CH₂)₂O | H | H | |
| H | H | —N(CH₂CH₂)₂NMe | H | 4-N(CH₂CH₂)₂O | 3-Cl | H | |
| H | H | —N(CH₂CH₂)₂NMe | H | 4-N(CH₂CH₂)₂NMe | 3-Cl | H | |

TABLE 1-continued

| | | | | | | |
|---|---|---|---|---|---|---|
| H | H | morpholine (–N⌒O) | H | 2-Me-4-N-piperazine-NMe | 3-Cl | H |
| H | H | –N-piperazine-NMe | H | 3-N-morpholine | 5-Me | H |
| H | H | –N-piperazine-NMe | H | 4-N-piperazine-NMe | 2-OMe | H |
| H | F | –N-piperazine-NMe | Cl | 4-N-piperazine-NMe | H | C$_2$H$_5$ |
| H | F | –N-piperazine-NMe | Cl | 4-N-piperazine-NMe | H | H |
| H | F | –N-piperazine-NMe | Cl | 4-N-morpholine | H | H |
| H | F | –N-piperazine-NMe | Cl | 3-N-morpholine | H | H | 134° C. |
| H | F | –N-piperazine-NMe | Cl | 2-N-morpholine | H | H | 126° C. |
| H | F | –N-morpholine | Cl | 4-N-piperazine-NMe | H | H |
| H | F | 2-Me-–N-piperazine-NMe | Cl | 4-N-piperazine-NMe | H | H |
| H | F | 2-Me-–N-piperazine-NH | Cl | 4-N-morpholine | H | H |
| H | F | –N-pyrrolidine-3-NMe$_2$ | Cl | 3-N-piperazine-NMe | H | H |

TABLE 1-continued
| | | | | | | |
|---|---|---|---|---|---|---|
| H | F | 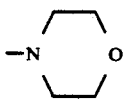 | Cl | 2-NNMe | H | H |
| H | F | 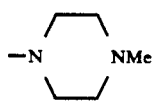NMe | Cl | 4-N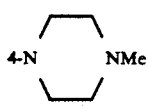NMe | 3-Cl | C₂H₅ |
| H | F | NMe | Cl | 4-NNMe | 3-Cl | H |
| H | F | 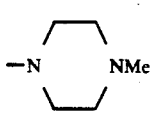NMe | Cl | 4-N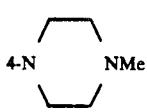NMe | 3-Cl | H |
| H | F | 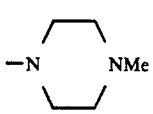NMe | Cl | 4-N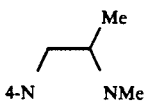NMe (Me) | 3-Cl | H |
| H | F | 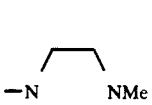NMe | Cl | 4-N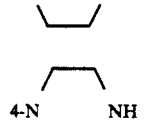NH | 3-Cl | H |
| H | F | 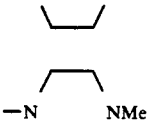NMe | Cl | 4-N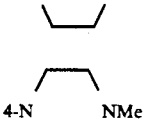NMe | 2-OCH₃ | H |
| H | F | 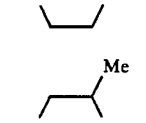NMe (Me) | Cl | 4-N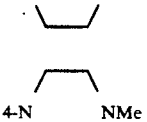NMe | 2-OCH₃ | H |
| H | F | O | Cl | 4-N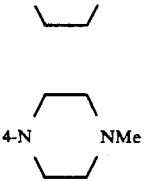NMe | 2-OCH₃ | H |
| H | F | NMe | Cl | 2-NNMe | 4-Me | H |
| H | F | 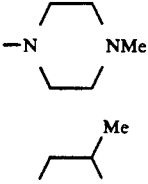NMe (Me) | Cl | 2-NNMe | 4-Me | H |
| H | F | 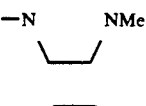NH | Cl | 2-N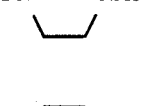NMe | 4-Me | H |
| H | F | 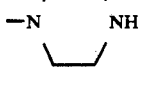O | Cl | 3-N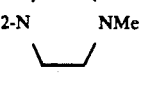O | 5-Me | H |

TABLE 1-continued
| | | | | | | |
|---|---|---|---|---|---|---|
| H | F | 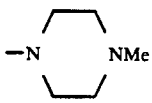 | Cl |  3-N...O e | 5-Me | H |
| H | F |  | Cl | 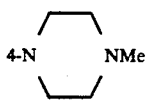 4-N...NMe | 5-O—OMe | H |
| H | F | 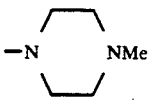 | Cl | 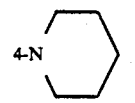 4-N | 3-CN | H |
| H | F | 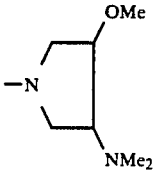 | Cl |  4-N...NMe | H | H |
| H | F | 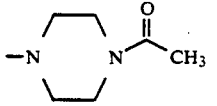 | Cl | 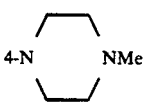 4-N...NMe | H | H |
| H | F | 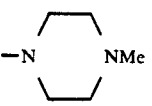 | Cl | 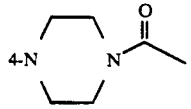 4-N | H | H |
| H | F | 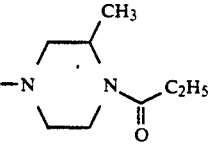 | Cl | 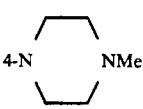 4-N...NMe | 3-Cl | H |
| H | F | 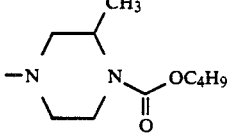 | Cl | 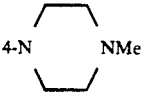 4-N...NMe | 3-Cl | H |
| H | F | 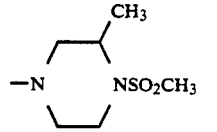 | Cl | 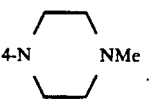 4-N...NMe | 3-Cl | H |
| H | F | 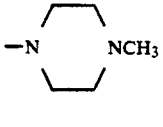 | Cl | 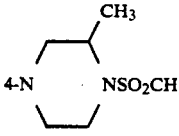 4-N...NSO$_2$CH$_3$ | 3-Cl | H |
| H | F | 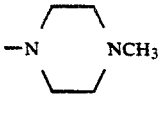 | Cl | 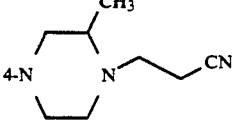 4-N | 3-Cl | H |

TABLE 1-continued
| | | | | | |
|---|---|---|---|---|---|
| H | F |  | Cl | 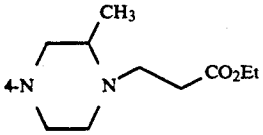 | 3-Cl H |
| H | F | 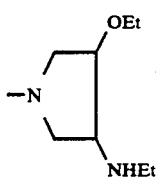 | Cl | 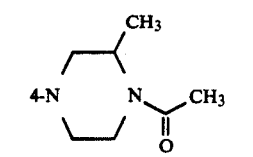 | 3-Cl H |
| H | F | 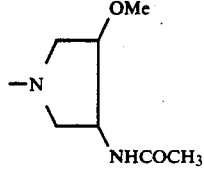 | Cl | 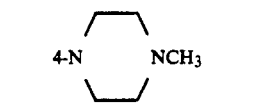 | 3-Cl H |
| H | F | 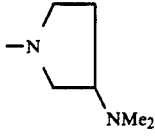 | Cl | 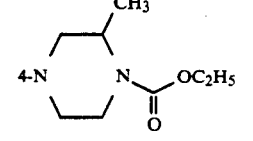 | 3-Cl H |
| H | NO$_2$ | 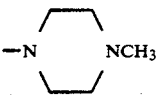 | H | 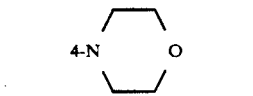 | H H |
| H | NO$_2$ | 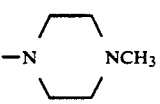 | H | 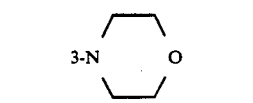 | H H |
| H | NO$_2$ | 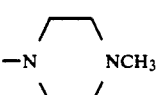 | H | 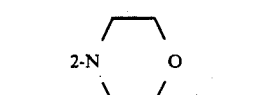 | H H |
| H | NO$_2$ | 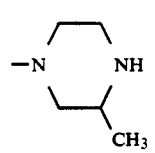 | H | 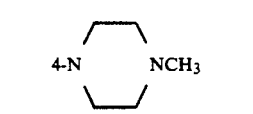 | 3-Cl H |
| H | NO$_2$ | 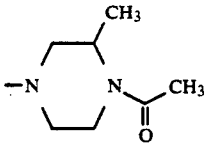 | H | 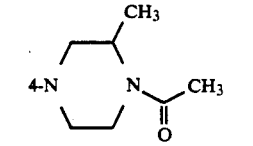 | 3-Cl H |
| H | NO$_2$ | 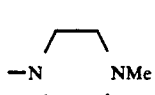 | H | 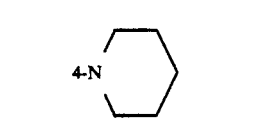 | 3-CN H |
| H | NO$_2$ | 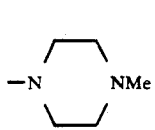 | H | 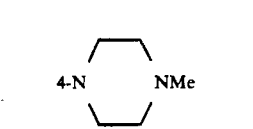 | 2-F H |

TABLE 1-continued

| | | | | | |
|---|---|---|---|---|---|
| H | NO$_2$ | −N⌬NMe (piperazine-NMe) | H | 4-N⌬NMe (piperazine-NMe) | 2-F | C$_2$H$_5$ |
| H | NO$_2$ | −N⌬NH with Me (2-methylpiperazine) | H | 4-N⌬NMe | 2-F | H |
| H | NO$_2$ | −N⌬NMe | H | 4-N⌬NH with Me (2-methylpiperazine) | 2-F | H |
| F | F | −N⌬NMe | F | 2-N⌬O (morpholine) | H | H |
| F | F | −N⌬NMe | F | 3-N⌬O | H | H |
| F | F | −N⌬NMe | F | 4-N⌬NMe | H | H |
| F | F | −N⌬NMe | F | 4-N⌬NMe | H | C$_2$H$_5$ |
| F | F | −N⌬NMe | F | 4-N⌬NMe | 3-Cl | H |
| F | F | −N⌬NMe | F | 2-N⌬NMe | 2-F | H |
| F | F | −N⌬NMe | F | 4-N⌬NMe with Me | 2-F | H |
| F | F | −N⌬NMe | F | 2-N⌬NH with Me | 2-F | H |
| F | F | −N⌬NMe | F | 2-N⌬NH with Me | 2-F | C$_2$H$_5$ |

TABLE 1-continued

| R¹ | R² | R³ | R⁴ | R⁵ | R⁶ | R⁷ |
|---|---|---|---|---|---|---|
| H | H | −N(piperazinyl)NCH₃ | H | 4-N(piperazinyl)NMe | 2-F | H |
| H | H | −N(piperazinyl)NCH₃ | H | 4-N(piperazinyl)NCH₃ | H | H |
| H | H | −N(piperazinyl)NCH₃ | H | 3-N(morpholinyl)O | H | H |
| H | H | −N(piperazinyl)NCH₃ | H | 2-N(piperazinyl)NCH₃ | H | H |
| H | H | −N(piperazinyl)NCH₃ | H | 4-N(2-methylpiperazinyl)NH | H | H |

R¹ = H, R² = F, R⁴ = H

| R³ | R⁵ | R⁶ | R⁷ | R⁸ | R⁹ | R |
|---|---|---|---|---|---|---|
| −N(piperazinyl)NCH₃ | 4-N(piperazinyl)NCH₃ | F | F | F | F | H |
| −N(piperazinyl)NCH₃ | 4-N(piperazinyl)NCH₃ | F | F | F | F | C₂H₅ |
| −N(3-NMe₂-pyrrolidinyl) | 4-N(2-methylpiperazinyl)NMe | F | F | F | F | H |
| −N(piperazinyl)NMe | 4-N(2-methylpiperazinyl)NCH₃ | F | F | F | F | H |
| −N(piperazinyl)NMe | 4-N(piperazinyl)NMe | 2-F | 3-F | H | H | H |
| −N(3-NMe₂-pyrrolidinyl) | 4-N(2-methylpiperazinyl)NMe | 2-F | 3-F | H | H | H |
| −N(piperazinyl)NCH₃ | 4-N(2-methylpiperazinyl)N-COCH₃ | 2-F | 3-F | H | H | H |

TABLE 1-continued

| R¹ | R² | R³ | R⁶ | R⁵ | R | ¹H-NMR (LM) or MS or m.p. |
|---|---|---|---|---|---|---|
| | | 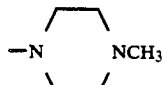 | 2-F | 5-F | H | H H H |

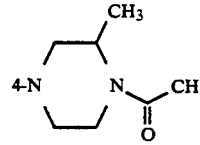

| R¹ | R² | R³ | R⁶ | R⁵ | R | ¹H-NMR (LM) or MS or m.p. |
|---|---|---|---|---|---|---|
| H | F | 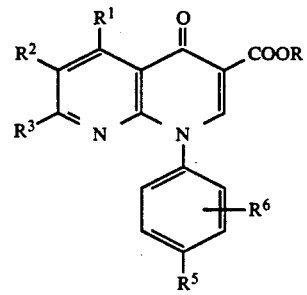 | o-F | = R³, 4-position | H | |
| | | 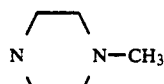 | " | " | " | |
| | | 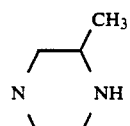 | " | " | " | |
| | | 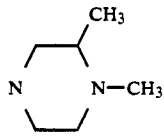 | " | " | " | |
| | | 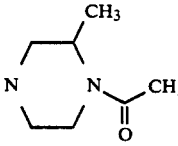 | " | " | " | |
| F | F | 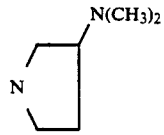 | o-F | = R³, 4-position | H | |
| H | F | | m-Cl | " | H | |
| H | F | | o-F | " | C₂H₅ | |
| H | Cl | | o-F | " | H | |

The compounds to be used according to the invention are valuable active compounds in human and veterinary medicine for the treatment or prophylaxis of diseases caused by viruses.

Examples of indication areas which can be mentioned in human medicine are:

1. The treatment or prophylaxis of human virus and retrovirus infections.
2. For the treatment or prophylaxis of diseases (AIDS) caused by HIV (human immuno-deficiency virus; earlier called HTLV III/LAV) and the stages associated therewith such as ARC (AIDS-related complex) and LAS (lymphadenopathy syndrome) and also the immuno-deficiency and encephalopathy caused by this virus.
3. For the treatment or the prophylaxis of an HTLV I or HTLV II infection.
4. For the treatment or prophylaxis of the AIDS-carrier state (AIDS-transmitter state).

Examples of indications in veterinary medicine which can be mentioned are:

Infections with
a) Maedi-visna (in sheep and goats)
b) progressive pneumonia virus (PPV) (in sheep and goats)
c) caprine arthritis encephalitis virus (in sheep and goats)
d) Zwoegerziekte virus (in sheep)
e) infectious anaemia virus (of the horse)
f) infections caused by the feline leukaemia virus.

The active compounds according to the invention can also be employed for the therapy and prophylaxis of diseases caused by influenza viruses.

The present invention includes pharmaceutical preparations which contain one or more compounds of the formula (I) or which consist of one or more active compounds of the formula (I) in addition to non-toxic, inert pharmaceutically suitable excipients, and processes for the production of these preparations.

The present invention also includes pharmaceutical preparations in dosage units. This means that the preparation is present in the form of individual parts, for example tablets, coated tablets, capsules, pills, suppositories and ampoules, whose active compound content correspond to a fragment or a multiple of an individual dose. The dosage units may contain, for example, 1, 2, 3 or 4 individual doses or ½, ⅓ or ¼ of an individual dose. An individual dose preferably contains the amount of active compound which is administered in one administration and which usually corresponds to a whole, a half, a third or a quarter of a daily dose.

Non-toxic, inert pharmaceutically suitable excipients are understood as meaning solid, semi-solid or liquid diluents, fillers and formulation auxiliaries of any type.

Preferred pharmaceutical preparations which may be mentioned are tablets, coated tablets, capsules, pills, granules, suppositories, solutions, suspensions and emulsions, pastes, ointments, gels, creams, lotions, powders and sprays. Tablets, coated tablets, capsules, pills and granules may contain the active compound or compounds in addition to the customary excipients, such as (a) fillers and extenders, for example starches, lactose, sucrose, glucose, mannitol, and silica,
(b) binders, for example carboxymethylcellulose, alginates, gelatine, polyvinylpyrrolidone,
(c) humectants, for example glycerol,
(d) disintegrants, for example agar-agar, calcium carbonate and sodium carbonate,
(e) solution retarding agents, for example paraffin and
(f) absorption accelerators, for example quaternary ammonium compounds,
(g) wetting agents, for example cetyl alcohol and glycerol monostearates,
(h) adsorption agents, for example kaolin and bentonite and
(i) lubricants, for example talc, calcium and magnesium stearate and solid polyethylene glycols or mixtures of these substances mentioned under (a) to (i).

The tablets, coated tablets, capsules, pills and granules can be provided with the customary coatings and shells which may contain opacifying agents, and may also be composed such that they deliver the active compounds, if desired with a delay, only or preferably to a certain part of the intestinal tract, it being possible to use, for example, polymer substances and waxes as embedding materials.

The active compound or compounds may optionally also be present in microencapsulated form with one or more of the abovementioned excipients.

Suppositories may contain the customary water-soluble or water-insoluble excipients, for example polyethylene glycols, fats, for example cocoa fat and higher esters (for example $C_{14}$-alcohol with $C_{16}$-fatty acid) or mixtures of these substances in addition to the active compound or compounds.

Ointments, pastes, creams and gels may contain the customary excipients, for example animal and vegetable fats, waxes, paraffins, starch, tragacanth, cellulose derivatives, polyethylene glycols, silicones, bentonites, silica, talc and zinc oxide or mixtures of these substances in addition to the active compound or compounds.

Powders and sprays may contain the customary excipients, for example lactose, talc, silica, hydrated alumina, calcium silicate and polyamide powder or mixtures of these substances in addition to the active compound or compounds. Sprays may additionally contain the customary propellants, for example chlorofluorohydrocarbons.

Solutions and emulsions may contain the customary excipients such as solvents, solubilizers and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cotton seed oil, groundnut oil, maize germ oil, olive oil, castor oil and sesame oil, glycerol, glycerol formal, tetrahydrofurfuryl alcohol, polyethylene glycols and fatty acid esters of sorbitan or mixtures of these substances in addition to the active compound or compounds.

For parenteral administration, the solutions and emulsions may also be present in sterile and bloodisotonic form.

Suspensions may contain the customary excipients such as liquid diluents, for example water, ethyl alcohol, propylene glycol, suspending agents, f or example ethoxylated isostearyl alcohols, polyoxyethylene sorbitol and sorbitan esters, microcrystalline cellulose, aluminium metahydroxide, bentonite, agar-agar and tragacanth or mixtures of these substances in addition to the active compound or compounds.

The formulation forms mentioned may also contain colorants, preservatives and odour- and flavour-improving additives, for example peppermint oil and eucalyptus oil and sweeteners, for example saccharine.

The active compounds of the formula (I) are intended to be present in the abovementioned pharmaceutical preparations, preferably in a concentration of about 0.1 to 99.5, preferably from about 0.5 to 95% by weight, of the total mixture.

The abovementioned pharmaceutical preparations may also contain other pharmaceutical active compounds in addition to the compounds of the formula (I).

The abovementioned pharmaceutical preparations are prepared in a customary manner by known methods, for example by mixing the active compound or compounds with the excipient or excipients.

The preparations mentioned can be used in humans and animals either orally, rectally, parenterally (intravenously, intramuscularly, subcutaneously), intracisternally, intravaginally, intraperitoneally, locally (powders, ointments, drops) and for the therapy of infections in hollow spaces and body cavities. Suitable preparations are injection solutions, solutions and suspensions for oral therapy, gels, pouring-on formulations, emulsions, ointments or drops. ophthalmological and dermatological formulations, silver salts and other salts, ear drops, eye ointments, powders or solutions may be used for local therapy. In the case of animals, administration can also be carried out via the feed or drinking water in suitable formulations. In addition, gels, powders, tablets, sustained-release tablets, premixes, concentrates, granules, pellets, tablets, boli, capsules, aerosols, sprays and inhalants can be used in humans and animals. The compounds according to the invention may additionally be incorporated into other excipient materials such as, for example, plastics, (plastic chains for local therapy), collagen or bone cement.

In general, it has proved advantageous both in human and in veterinary medicine to administer the active compound or compounds of the formula (I) in total amounts from about 0.5 to about 500, preferably 5 to 100 mg/kg of body weight every 24 hours, if desired in the form of several individual doses, in order to achieved the desired results. An individual dose contains the active compound or compounds preferably in amounts from about 1 to about 80, in particular 3 to 30 mg/kg of body weight. However, it may be necessary to deviate from the dosages mentioned, in particular depending on the species and the body weight of the subject to be treated, the type and severity of the disease, the type of preparation and the administration of the medicoment and the period or interval within which administration takes place.

Thus, in some cases it may be sufficient to manage with less than the abovementioned amount of active compound, while in other cases the abovementioned amount of active compound must be exceeded. The optimum dosage necessary in each case and the manner of administration of the active compounds can easily be determined by any person skilled in the art on the basis of his expert knowledge.

The compounds to be used according to the invention can be given in the customary concentrations and preparations together with the food or with food preparations or with the drinking water.

The following examples illustrate the invention.

EXAMPLE 1

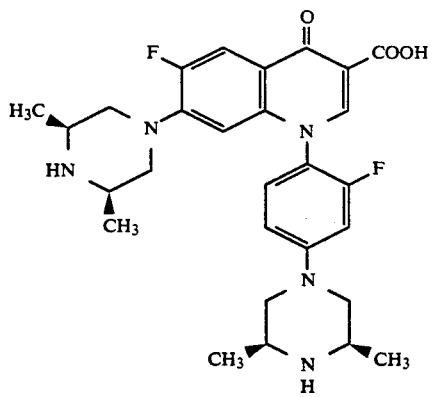

500 mg (1.4 mmol) of 1-(2,4-difluorophenyl)-6-fluoro-7-chloro-1,4-dihydro-4-oxo-3-quinolinecarboxylic acid, 4 ml of dimethyl sulphoxide and 640 mg (5.6 mmol) of cis-2,6-dimethylpiperazine are heated at 140° C. for 2 hours. The mixture is evaporated, and the residue is dissolved in water and extracted once with methylene chloride. The aqueous phase is evaporated, and the residue is triturated with ethanol, filtered off with suction and dried.

Yield: 60 mg (8% of theory) of 1-(2-fluoro-3-(cis-3,5-dimethylpiperazinyl)-phenyl)-6-fluoro-7-(cis-3,5-dimethylpiperazinyl)-1,4-dihydro-4-oxo-3-quinolinecarboxylic acid.

Melting point: 180°–182° C. (with decomposition).

EXAMPLE 2

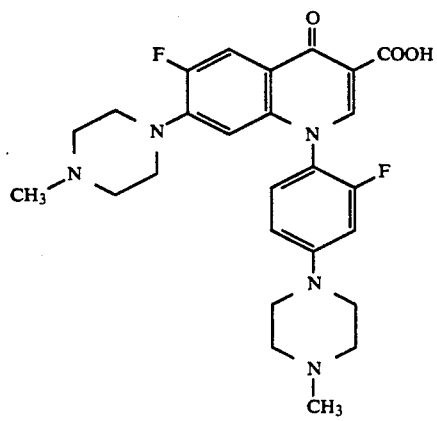

The reaction is carried out analogously to Example 1 using 1-methylpiperazine, after evaporating the reaction mixture the residue is dissolved in methylene chloride and washed twice with water and the organic phase is evaporated and chromatographed on 40 g of silica gel. (Eluent: acetonitrile:water:glacial acetic acid 5:1:1 (v:v:v)).

Yield: 190 mg (54% of theory) of 1-(2-fluoro-4-(4-methylpiperazinyl)-phenyl)-6-fluoro-7-(4-methylpiperazinyl)-1,4-dihydro-4-oxo-3-quinolinecarboxylic acid.

$^1$H-NMR spectrum (CDCl$_3$): 2.34 (S, 3H); 2.40 (S, 3H) 2.54 (T, 4H); 2.61 (T, 4H); 6.40 (D, 1H); 6.80 (M, 2H) 7.24 (T, 1H); 8.07 (D, 1H); 8.60 (S, 1H) ppm.

EXAMPLE 3

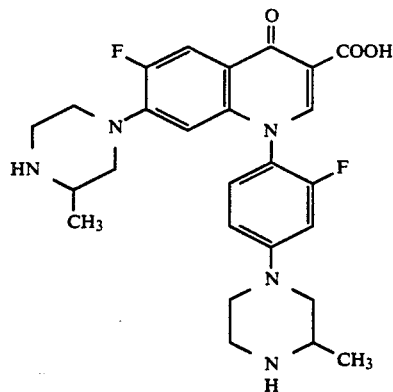

The reaction is carried out analogously to Example 1 using 2-methylpiperazine.

Yield: 291 mg (41% of theory) of 1-(2-fluoro-4-(3-methylpiperazinyl)-phenyl)-6-fluoro-7-(3-methylpiperazinyl)-1,4-dihydro-4-oxo-3-quinolinecarboxylic acid.

Melting point: 273°–281° C. (with decomposition)

EXAMPLE 4

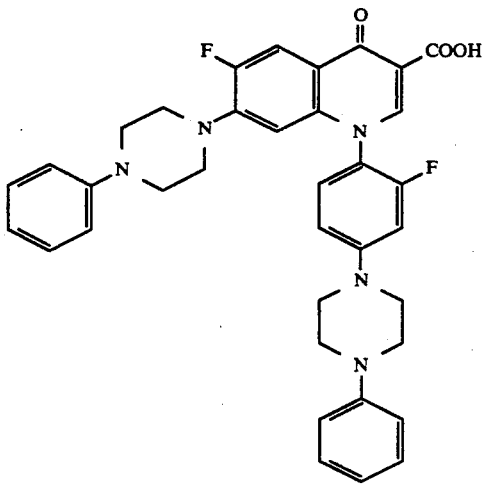

The reaction is carried out analogously to Example 1 using 1-phenylpiperazine. After evaporating the reaction mixture, the residue is boiled with toluene and filtered, the filter residue is dissolved in methylene chloride, washed twice with water and concentrated, and the residue is dried.

Yield: 507 mg (58% of theory) of 1-(2-fluoro-4-(4-phenylpiperazinyl)-phenyl)-6-fluoro-7-(4-phenyl-piperazinyl)-1,4-dihydro-4-oxo-3-quinolinecarboxylic acid.

Melting point: 138°-140° C.

EXAMPLE 5

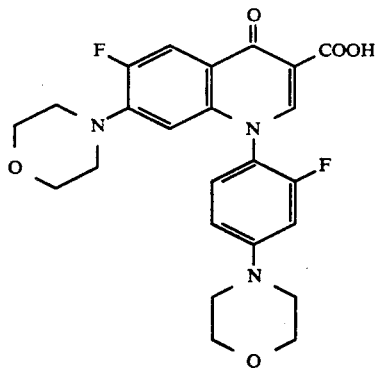

The reaction is carried out analogously to Example 1 using morpholine.

Yield: 402 mg (60% of theory) of 1-(2-fluoro-4-(morpholinylphenyl)-6-fluoro-7-morpholinyl-1,4-dihydro-4-oxo-3-quinolinecarboxylic acid.

Melting point: 273° C. (methylene chloride, n-hexane) (with decomposition).

EXAMPLE 6

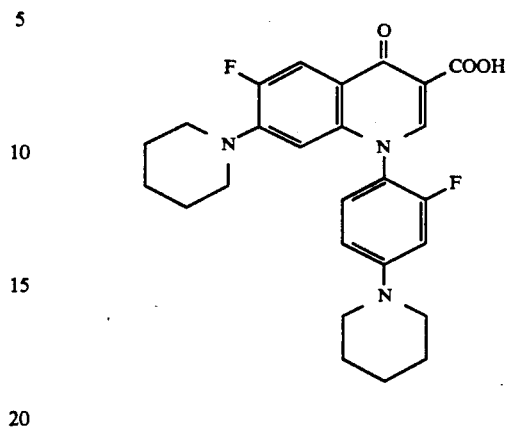

The reaction is carried out analogously to Example 1 using piperidine.

Yield: 404 mg (61% of theory) of 1-(2-fluoro-4-(piperidinylphenyl)-6-fluoro-7-piperidinyl-1,4-dihydro-4-oxo-3-quinolinecarboxylic acid.

Melting point: 223° C. (methylene chloride, n-hexane) (with decomposition).

EXAMPLE 7

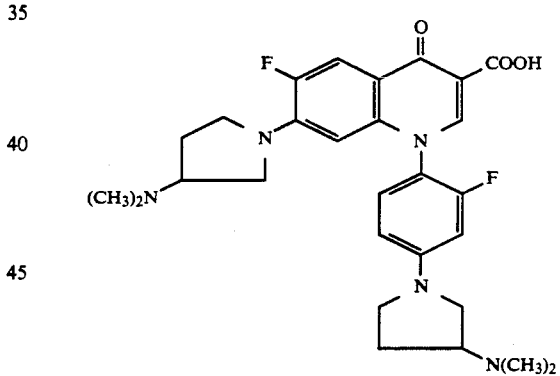

The reaction is carried out analogously to Example 1 using 3-dimethylaminopyrrolidine. After evaporating the reaction mixture, the residue is boiled with toluene, the combined toluene phase is washed three times with water and evaporated, and the residue is dissolved in methylene chloride and precipitated by adding n-hexane.

Yield: 304 mg (41% of theory) of 1-(2-fluoro-4-(3-(dimethylamino)pyrrolidinyl)-phenyl-6-fluoro-7-(3-(dimethylaminopyrrolidinyl)-1,4-dihydro-4-oxo-3-quinolinecarboxylic Melting point: 190° C.

EXAMPLE 8

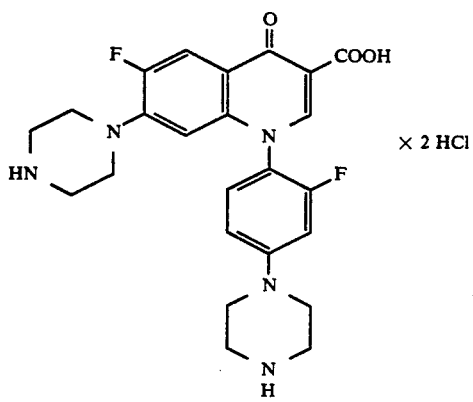

A) 150 g (43.5 mmol) of 1-(2,4-difluorophenyl)-6-fluoro-7-chloro-1,4-dihydro-4-oxo-3-quinolinic acid, 100 ml of dimethyl sulphoxide and 14.6 g (170 mmol) of anhydrous piperazine are heated at 140° C. for two hours. The product subsequently precipitates in the course of three days at room temperature, and is filtered off with suction and washed with ice-cold water.

Yield: 9.9 g (50% of theory) of 1-(2-fluoro-4-piperazinylphenyl)-6-fluoro-7-piperazinyl-1,4-dihydro-4-oxo-3-quinolinecarboxylic acid.

Melting point: 207–209° C.

B) 500 mg (1.1 mol) of the product from step A are dissolved in 5 ml of 3N hydrochloric acid, the solution is evaporated, and the residue is triturated with ethanol, filtered off with suction and dried.

Yield: 325 mg (60% of theory) of 1-(2-fluoro-4-piperazinylphenyl)-6-fluoro-7-piperazinyl-1,4-dihydro-4-oxo-3-quinolinecarboxylic acid dihydrochloride.

Melting point: >250° C. (with decomposition),

EXAMPLE 9

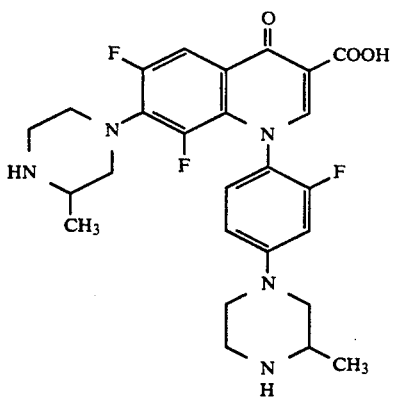

1.0 g (2.9 mmol) of 1-(2,4-difluorophenyl)-6,7,8-trifluoro-1,4-dihydro-4-oxo-3-quinolinic acid, 12 ml of dimethyl sulphoxide and 1.2 g (11.8 mmol) of 2-methylpiperazine are heated at 140° C. for two hours and evaporated, and the residue is chromatographed on 80° C. of silica gel (eluent: methylene chloride:methanol:20% strength aqueous ammonia solution=4:8:1), product-containing fractions are evaporated, the residue is dissolved in methanol and precipitated using n-hexane.

Yield: 104 mg (7% of theory) of 1-(2-fluoro-4-(3-methylpiperazinyl)-phenyl)-6,8-difluoro-7-(3-methyl-piperazinyl)-1,4-dihydro-4-oxo-3-quinolinecarboxylic acid.

Melting point: 250° C. (with decomposition)

EXAMPLE 10

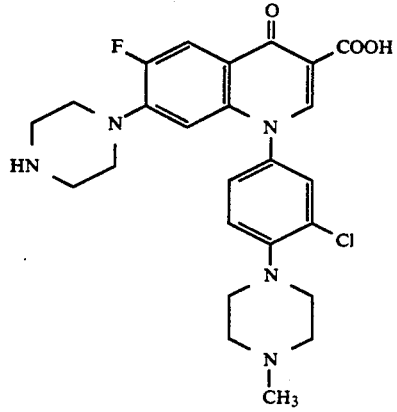

450 mg (1.0 mmol) of 1-(3-chloro-4-(4-methyl-piperazinyl)-phenyl-6-fluoro-7-chloro-1,4-dihydro-4-oxo-3-quinolinic acid, 4 ml of acetonitrile, 2 ml of N,N-dimethylformamide, 172 mg (2.0 mmol) of piperazine and 336 mg (3.0 mmol) of DABCO are heated to 120° C. for 24 hours and then evaporated. The residue is boiled with toluene, the toluene phase is evaporated, the residue is dissolved in methylene chloride and the solution is washed twice with water. The methylene chloride phase is evaporated and the residue is chromatographed on 500 g of silica gel (eluent: acetonitrile:-water:glacial acetic acid=5:1:1 (v:v:v)).

Yield: 123 mg (25% of theory) of 1-(3-chloro-4-(4-methylpiperazinyl)-phenyl)-6-fluoro-7-piperazinyl)-1,4-dihydro-4-oxo-3-quinolinecarboxylic acid.

Melting point: 230° C. (with decomposition).

EXAMPLE 11

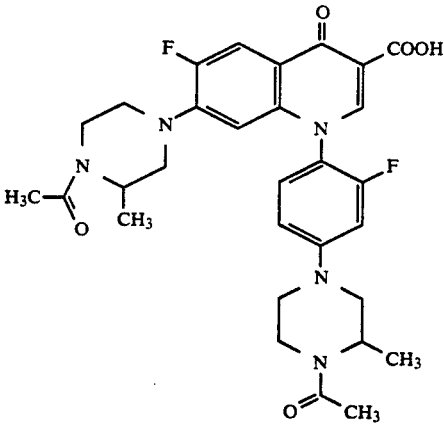

248 mg (0.5 =mmol) of 1-(2-fluoro-4-(3-methyl-piperazinyl)-phenyl-6-fluoro-7-(3-methylpiperazinyl)-1,4-dihydro-4-oxo-3-quinolinic acid, 204 mg (2.0 mmol) of acetic anhydride and 15 ml of pyridine are allowed to react at 0° C. for two hours, and the mixture is warmed to room temperature and evaporated. Toluene is added twice to the reaction mixture and evaporated, the residue is then dissolved in methylene chloride, the solution is washed twice with water and evaporated and the residue is dried.

Yield: 277 mg (95% of theory) of 1-(2-fluoro-4-(3-methyl-4-acetylpiperazinyl)-phenyl)-6-fluoro-7-(3-methyl-4-acetylpiperazinyl)-1,4-dihydro-4-oxo-3-quinolinecarboxylic acid $R_F$: 0.23 (silica gel: acetonitrile:water:glacial acetic acid=150:10:1).

EXAMPLE 12

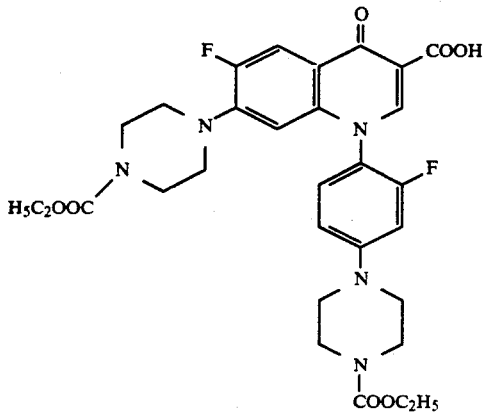

234 mg of 1-(2-fluoro-4-piperazinyl-phenyl)-6-fluoro-7-piperazinyl-1,4-dihydro-4-oxo-3-quinolinic acid are reacted with 141 g (1.3 mmol) of chloroformic acid analogously to Example 11.

Yield: 286 mg (89% of theory) of ethyl 1-(2-fluoro-4-(4-carbethoxypiperazinyl)-phenyl)-6-fluoro-7-(4-carbethoxypiperazinyl)-1,4-dihydro-4-oxo-3-quinolinecarboxylate.

Mass spectrum: m/e=641 (M+), 569 (100%, M+-CO₂C₂H₅), 467, 56, 29.

EXAMPLE 13

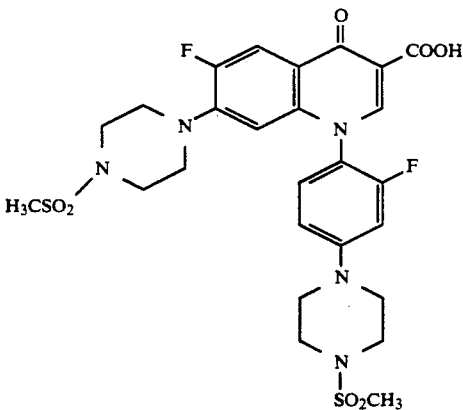

234 mg (0.5 mmol) of 1-(2-fluoro-4-piperazinyl-phenyl)-6-fluoro-7-piperazinyl-1,4-dihydro-4-oxo-3-quinolinic acid are reacted with 286 mg (2–5 mmol) of methanesulphonyl chloride analogously to Example 11.

Yield: 114 mg (36% of theory) of 1-(2-fluoro-4-(4-methylsulphonylpiperazinyl)-phenyl)-6-fluoro-7-(4-methylsulphonylpiperazinyl)-1,4-dihydro-4-oxo-3-quinolinecarboxylic acid.

Melting point: 178° C. (with decomposition).

EXAMPLE 14

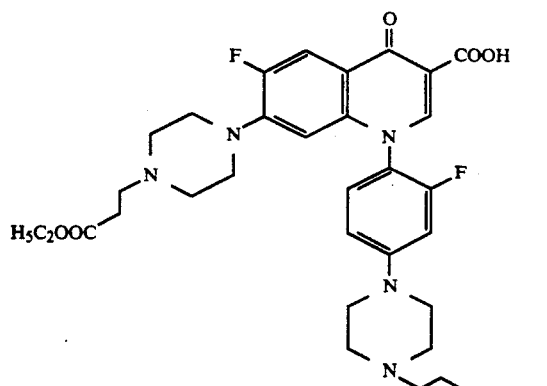

469 mg (1.0 mmol) of 1-(2-fluoro-4-piperazinyl-phenyl)-6-fluoro-7-piperazinyl-1,4-dihydro-4-oxo-3-quinolinecarboxylic acid, 9 ml of water, 4.5 ml of ethanol and 1.0 g (10 mmol) of ethyl acrylate are stirred at 25° C. for 3 days and evaporated, the residue is dissolved in methylene chloride and the solution is washed twice with water. The organic phase is evaporated and dried.

Yield: 445 mg (61% of theory) of 1-(2-fluoro-4-(4-carboxyeth-2-yl -piperazinyl)-phenyl)-6-fluoro-7-(4-carboxyeth-2-yl-piperazinyl)-1,4-dihydro-4-oxo-3-quinolinecarboxylic acid.

¹H-NMR spectrum (CF₃COOD): 1.37 (2T,3H); 3.16 (2T,4H); 3.16 (2T,4H); 3.56 (2T,BH); 3,77 (2T,4H); 4.06 (M,8H); 4.37 (2Q,4H); 6.94 (D,1H); 7.10 (M,2H); 7.60 (T,1H); 8.40 (D,1H); 9.20 (S,1H) PPM.

EXAMPLE 15

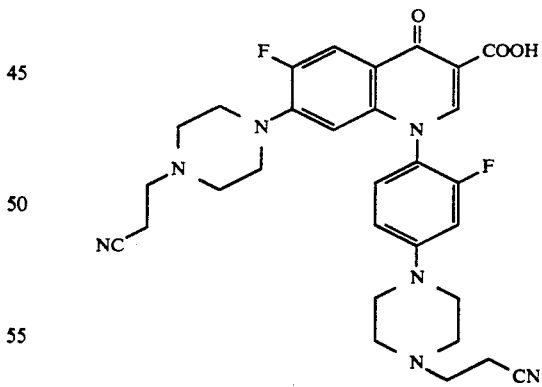

The reaction is carried out analogously to Example 14 using acrylonitrile.

Yield: 396 mg (69% of theory) of 1-(2-fluoro-4-(4-cyanoeth-2-yl-piperazinyl)-phenyl)-6-fluoro-7-(4-cyanoeth-2-yl-piperazinyl)-1,4-dihydro-4-oxo-3-quinolinecarboxylic acid.

¹H-NMR spectrum (CF₃COOD): 3.30 (2T,3H); 3.60 (M,8H); 3.87 (2T,4H); 4.10 (M,8H); 6.97 (D,1H); 7.10 (M,2H); 7.60 (T,1H); 8.40 (D,1H); 9.20 (S,1H) ppm.

EXAMPLE 16

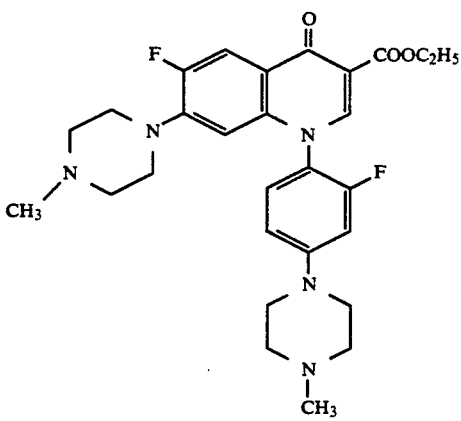

560 mg (1.4 mmol) of ethyl 1-(2,4-difluorophenyl)-6,7-difluoro-1,4-dihydro-4-oxo-3-quinolinecarboxylate, 6 ml of dimethyl sulphoxide and 550 mg (5.5 mmol) of N-methylpiperazine are heated at 140° C. for two hours. The mixture is evaporated, the residue is dissolved in methylene chloride and the solution is washed twice with water. After evaporating, the residue is chromatographed on 100 g of silica gel (eluent first toluene:ethanol 1:1, then ethanol:toluene:glacial acetic acid=100:100:1). The product-containing fractions were concentrated and dried.

Yield: 300 mg (42% of theory) of ethyl 1-(2-fluoro-4-(methylpiperazinyl)-phenyl)-6-fluoro-7-(4-methyl-piperazinyl)-1,4-dihydro-4-oxo-3-quinolinecarboxylate, acetic acid salt.

Melting point: 58° C.

USE EXAMPLES

It was surprisingly found in the context of the investigations which led to the present invention that the compound of the general formula (I) to be used according to the invention has an exceptionally strong action against retroviruses. This is illustrated by way of example for the compound on the visna virus in cell cultures by the experimental data given further below. The visna virus and the HIV virus (human immunodeficiency virus) both belong to the retrovirus subfamily of the lentiviruses [Haase A. T. Nature (1986) 322, 130-136]. Both viruses have a similar genome organization and a complex transcription pattern compared to the other retroviruses [Sojijo P. et al., Cell (1985), 42, 369-382; Davis J. L. et al., Journal of Virolocjy (1987) 61, pp. 1325-1331).

Moreover, it has been shown [Frank, K. B. , et al. , Antimicrobial Agents and Chemotherapy (1987) 32 (9), pp. 1369-1374] that known inhibitors of HIV also inhibit the visna virus in vitro in comparable concentrations; i.e. this model is suitable for the testing and discovery of inhibitors of HIV.

In cell cultures which have been infected with visna virus, pronounced virus-induced cytopathic effects occur 5 to 10 days after the infection. It was possible to prevent the occurrence of these cytopathic effects by treatment of the infected cell cultures with the compound according to the invention.

The visna virus test was carried out by the method of O. Narayan et al., Journal of Infectious Diseases 135, 5, 1977, 800-806. For this purpose, the compound according to the invention was diluted in culture medium in non-cytotoxic concentrations in 96-well microtitre plates. Sheep fibroblast cells ($5 \times 10^4$ cells per well) in production medium were then added to each well. Each well was then filled with 50 μl of a visna virus solution having a titre of about $2.5 \times 10^4$ TCID$_{50}$ (TCID=tissue culture infectious dose). This virus dose corresponds to an MOI (multiplicity of infection) of about 0.05.

Under these infection conditions, a virus-induced cytopathic effect resulted between day 5 and day 10 in one infection control without substance. The infected and treated cells and the control cells were incubated at 37° C. 5% $CO_2$ for 7 days.

On occurrence of the virus-induced cytopathogenic effect in the untreated virus control, the cultures were fixed with formalin and then stained using a Giemsa solution. The inhibitory concentration (IC$_{50}$) was determined microscopically as the concentration at which the cytopathic effect was inhibited by 50% in comparison to th& untreated virus control, which exhibited 100% cell destruction.

It was found that the visna virus-infected cells were protected from the virus-induced cell destruction using the compounds according to the invention. This is shown as an example with the aid of the data for the following compounds:

TABLE

| Compound according to the invention | Inhibition of infectious visna virus [μg/ml] |
| --- | --- |

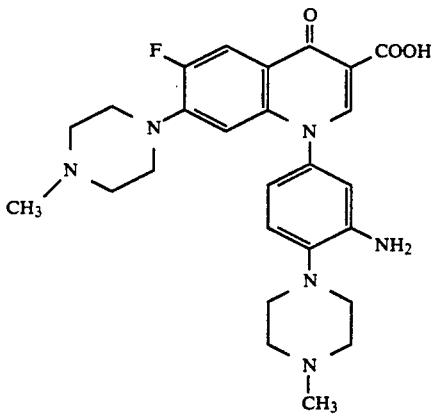

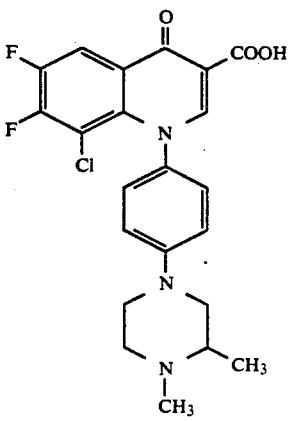

TABLE-continued

| Compound according to the invention | Inhibition of infectious visna virus [μg/ml] |
|---|---|
| 6-F, 7-(4-methylpiperazin-1-yl), 1-[2-fluoro-4-(4-methylpiperazin-1-yl)phenyl]-4-oxo-quinoline-3-carboxylic acid | 12 |
| 6-F, 8-F, 7-(4-methylpiperazin-1-yl), 1-[2-fluoro-4-(4-methylpiperazin-1-yl)phenyl]-4-oxo-quinoline-3-carboxylic acid | 50 |
| 6-F, 7-[4-(1-acetyl-2-methyl)piperazin-1-yl ethyl-acetamido], 1-[2-fluoro-4-(3-methyl-4-acetylpiperazin-1-yl)phenyl]-4-oxo-quinoline-3-carboxylic acid | 25 |
| 6-F, 7-(N,N-diethylamino), 1-[4-(4-methylpiperazin-1-yl)phenyl]-4-oxo-quinoline-3-carboxylic acid | 25 |
| 6-F, 7-(N,N-diethylamino), 1-[4-morpholinophenyl]-4-oxo-quinoline-3-carboxylic acid | 12 |
| 6-F, 7-F, 8-Cl, 1-[2-(4-methylpiperazin-1-yl)phenyl]-4-oxo-quinoline-3-carboxylic acid ethyl ester | 12 |
| 6-F, 7-(4-methylpiperazin-1-yl), 1-[4-(3-methylpiperazin-1-yl)phenyl]-4-oxo-quinoline-3-carboxylic acid | 50 |

TABLE-continued

| Compound according to the invention | Inhibition of infectious visna virus [μg/ml] |
|---|---|
| [Structure: 6-fluoro-7-(4-methylpiperazin-1-yl)-1-[2,3-difluoro-4-(4-methylpiperazin-1-yl)phenyl]-4-oxo-quinoline-3-carboxylic acid] | 50 |
| [Structure: 6-fluoro-7-morpholino-8-chloro-1-[3-amino-4-(4-methylpiperazin-1-yl)phenyl]-4-oxo-quinoline-3-carboxylic acid] | 6 |
| [Structure: 6-fluoro-7-di(n-C₃H₅)amino-1-[3-amino-4-(2-methylpiperazin-1-yl)phenyl]-4-oxo-quinoline-3-carboxylic acid] | 0.5 |
| [Structure: 6-fluoro-7-di(n-C₃H₅)amino-1-[2,3-difluoro-4-(4-methylpiperazin-1-yl)phenyl]-4-oxo-quinoline-3-carboxylic acid] | 0.5 |

We claim:

1. A compound of the formula $$\begin{array}{c} R^1 \\ R^2 \\ \text{Halogen} \\ R^4 \end{array} \begin{array}{c} O \\ \parallel \\ \text{CO}_2R \\ N \\ R^5 \end{array}$$

$$R^9 - \begin{array}{c} \\ \\ \end{array} - R^6$$

$$R^8 \quad R^7$$

in which

R is hydrogen or alkyl having 1–4 carbon atoms,

R¹ is hydrogen, amino, alkylamino having 1 to 4 carbon atoms, dialkylamino having 1 to 3 carbon atoms per alkyl group, hydroxyl, alkoxy having 1 to 4 carbon atoms, mercapto, alkylthio having 1 to 4 carbon atoms, arylthio, halogen, cyano or nitro, R² is hydrogen, nitro or halogen, R⁵ is a group of the formula (II)

$$\begin{array}{c} R^{11} \quad R^{12} \\ R^{10} \diagup \diagdown R^{13} \\ -N \quad W \\ R^{17} \diagup \diagdown R^{14} \\ R^{16} \quad R^{15} \end{array} \quad (II)$$

in which

W is O, S, NR¹⁸ or CR¹⁹R²⁰ and

R⁶, R⁷, R⁸ and R⁹ are identical or different and each is hydrogen, alkyl having 1 to 5 carbon atoms, nitro, amino, monoalkylamino having 1–3 C atoms, dialkylamino having 1–6 C atoms, O-alkyl having 1–5 carbon atoms, S-alkyl having 1–5 carbon atoms, trifluoromethyl, cyano or halogen, R¹⁸ is H, (C$_1$–C$_{10}$)-alkyl or (C$_3$–C$_6$)-cycloalkyl optionally substituted by one or more substituents selected from the group consisting of Hal, OH, CN, COOAlkyl(C$_1$–C$_7$) or OAlkyl, aryl (C$_6$–C$_{12}$) optionally substituted by halogen, o-alkyl (C$_1$–C$_2$) or (C$_1$–C$_4$)-alkyl,

CN,

COOalkyl(C$_1$–C$_4$),

C$_1$–C$_4$-acyl or

Alkyl (C$_1$–C$_4$)-sulphonyl,

R$^{10}$, R$^{11}$, R$^{12}$, R$^{13}$, R$^{14}$, R$^{15}$, R$^{16}$, R$^{17}$, R$^{19}$ and R$^{20}$ are identical or different and each is hydrogen, C$_1$–C$_3$ alkyl or C$_3$–C$_6$-cycloalkyl optionally substituted by one or more halogens, OH, O-alkyl (C$_1$–C$_6$), alkyl (C$_1$–C$_4$), CN or COO alkyl (C$_1$–C$_6$), hydroxyl, or amino, alkylamino having 1–4 carbon atoms, dialkylamino having 1–3 carbon atoms per alkyl group or phenyl which is optionally substituted by halogen, and R$^4$ is hydrogen, halogen, methyl, cyano, nitro, methoxy or amine, or a pharmaceutically acceptable derivative thereof.

2. A compound according to claim 1, wherein such compound is 1-[3-chloro-4-(4-methylpiperazinyl)-phenyl]-7-chloro-6-fluoro-1,4-dihydro-4-oxo-3-quinoline carboxylic acid.

3. A compound according to claim 1, wherein such compound is 1-[4-(3,4-dimethylpiperazinyl)-phenyl]-6,7-difluoro-8-chloro-1,4-dihydro-4-oxo-3-quinoline carboxylic acid.

4. A compound according to claim 1, wherein such compound is 1-[2-(4-methylpiperazinyl)-phenyl]-6,7-difluoro-8-chloro-1,4-dihydro-4-oxo-3-quinoline carboxylic acid.

* * * * *